US011395489B2

(12) United States Patent
Rendine et al.

(10) Patent No.: US 11,395,489 B2
(45) Date of Patent: Jul. 26, 2022

(54) MICROBIOCIDAL PICOLINAMIDE DERIVATIVES

(71) Applicant: Syngenta Participations AG, Basel (CH)

(72) Inventors: Stefano Rendine, Stein (CH); Clemens Lamberth, Stein (CH); Renaud Beaudegnies, Stein (CH); Mattia Riccardo Monaco, Stein (CH)

(73) Assignee: Syngenta Participations AG, Basel (CH)

( * ) Notice: Subject to any disclaimer, the term of this patent is extended or adjusted under 35 U.S.C. 154(b) by 19 days.

(21) Appl. No.: 16/753,702

(22) PCT Filed: Oct. 4, 2018

(86) PCT No.: PCT/EP2018/077001

§ 371 (c)(1),
(2) Date: Apr. 3, 2020

(87) PCT Pub. No.: WO2019/068812

PCT Pub. Date: Apr. 11, 2019

(65) Prior Publication Data

US 2020/0267977 A1 Aug. 27, 2020

(30) Foreign Application Priority Data

Oct. 5, 2017 (EP) .................................... 17195040

(51) Int. Cl.
*A01N 43/40* (2006.01)
*C07D 213/81* (2006.01)

(52) U.S. Cl.
CPC ........... *A01N 43/40* (2013.01); *C07D 213/81* (2013.01)

(58) Field of Classification Search
CPC .................................................... C07D 213/81
USPC .......................................................... 514/350
See application file for complete search history.

(56) References Cited

U.S. PATENT DOCUMENTS

| | | | | |
|---|---|---|---|---|
| 10,111,432 | B2 * | 10/2018 | Rigoli | C07D 213/83 |
| 10,595,531 | B2 * | 3/2020 | Bravo-Altamirano | C07D 409/14 |
| 2018/0186743 | A1 * | 7/2018 | Loy | C07C 271/22 |

FOREIGN PATENT DOCUMENTS

| | | | |
|---|---|---|---|
| WO | 2016109288 | A1 | 7/2016 |
| WO | 2016109300 | A1 | 7/2016 |
| WO | 2016122802 | A1 | 8/2016 |

OTHER PUBLICATIONS

International Search Report and Written Opinion for Intenational Patent Applications No. PCT/EP2018/077001 dated Nov. 7, 2018.
European Search Report for European Patent Application No. 17195040.5 dated Dec. 18, 2017.

* cited by examiner

*Primary Examiner* — Taofiq A Solola
(74) *Attorney, Agent, or Firm* — BakerHostetler; Toni-Junell Herbert

(57) ABSTRACT

Compounds of the formula (I) wherein the substituents are as defined in claim 1, useful as pesticides, and especially fungicides.

(I)

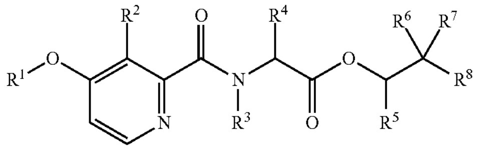

14 Claims, No Drawings

MICROBIOCIDAL PICOLINAMIDE DERIVATIVES

CROSS-REFERENCE TO RELATED APPLICATIONS

This application is a 371 National Stage application of International Application No. PCT/EP2018/077001 filed Oct. 4, 2018 which claims priority to EP 17195040.5, filed Oct. 5, 2017, the entire contents of which applications are hereby incorporated by reference.

The present invention relates to microbiocidal picolinamide derivatives, e.g., as active ingredients, which have microbiocidal activity, in particular fungicidal activity. The invention also relates to the preparation of these picolinamide derivatives, to agrochemical compositions which comprise at least one of the picolinamide derivatives and to uses of the picolinamide derivatives or compositions thereof in agriculture or horticulture for controlling or preventing the infestation of plants, harvested food crops, seeds or non-living materials by phytopathogenic microorganisms, preferably fungi.

Picolinamide compounds as fungicidal agents are described in WO 2016/109288, WO 2016/109289, WO 2016/109300, WO 2016/109301, WO 2016/109302 and WO 2016/109303.

According to the present invention, there is provided compound of formula (I):

(I)

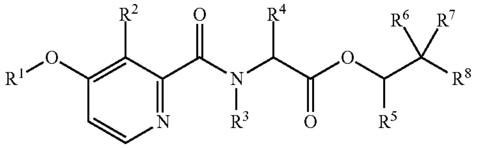

wherein, $R^1$ is $C_1$-$C_{12}$alkyl or $C_1$-$C_6$haloalkyl;

$R^2$ is hydroxy, $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy or $C_2$-$C_6$acyloxy$C_1$-$C_6$haloalkoxy;

$R^3$ is hydrogen, $C_1$-$C_6$alkyl, $C_1$-$C_6$alkoxy or $C_3$-$C_8$cycloalkyl;

$R^4$ and $R^5$ are independently $C_1$-$C_{12}$alkyl, $C_3$-$C_8$cycloalkyl, $C_1$-$C_6$haloalkyl, $C_1$-$C_6$alkoxy$C_1$-$C_6$alkyl or $C_3$-$C_8$halocycloalkyl;

$R^6$ and $R^7$ are independently $C_1$-$C_6$alkyl or $C_3$-$C_8$cycloalkyl; or $R^6$ and $R^7$ together with the carbon atom to which they are attached form a $C_3$-$C_8$cycloalkyl ring which is optionally substituted by 1, 2 or 3 substituents, which may be the same or different, selected from $R^9$, or is optionally substituted by a single substituent which is $R^{10}$, or is optionally substituted by 1 or 2 substituents, which may be the same or different, selected from $R^9$ and a single substituent which is $R^{10}$;

$R^8$ is phenyl, phenoxy, naphthyl, naphthyloxy, heteroaryl or heteroaryloxy, wherein the heteroaryl moiety is a 5- or 6-membered aromatic ring which comprises 1, 2, 3 or 4 heteroatoms individually selected from N, O and S, heterodiaryl or heterodiaryloxy, wherein the heterodiaryl moiety is a 9- or 10-membered bicyclic aromatic system which comprises 1, 2, 3 or 4 heteroatoms individually selected from N, O and S, wherein each phenyl, naphthyl, heteroaryl or heterodiaryl is optionally substituted by 1, 2 or 3 substituents, which may be the same or different, selected from $R^9$;

$R^9$ is halogen, cyano, $C_1$-$C_4$alkyl, $C_1$-$C_4$haloalkyl, $C_1$-$C_4$alkoxy, $C_1$-$C_4$haloalkoxy; and $R^{10}$ is phenyl or cyclopropyl each optionally substituted by 1, 2 or 3 substituents, which may be the same or different, selected from fluoro, chloro, bromo, cyano, methyl, ethyl, difluoromethyl, trifluoromethyl, methoxy, ethoxy, difluoromethoxy, trifluoromethoxy; or a salt or an N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I) according to the present invention. Such an agricultural composition may further comprise at least one additional active ingredient and/or an agrochemically-acceptable diluent or carrier.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

Where substituents are indicated as being "optionally substituted", this means that they may or may not carry one or more identical or different substituents, e.g., one, two or three, etc, $R^9$ or $R^{10}$ substituents. For example, $C_1$-$C_6$alkyl substituted by 1, 2 or 3 halogens, may include, but not be limited to, $—CH_2Cl$, $—CHCl_2$, $—CCl_3$, $—CH_2F$, $—CHF_2$, $—CF_3$, $—CH_2CF_3$ or $—CF_2CH_3$ groups. As another example, $C_1$-$C_6$alkoxy substituted by 1, 2 or 3 halogens, may include, but not be limited to, $CH_2ClO—$, $CHCl_2O—$, $CCl_3O—$, $CH_2FO—$, $CHF_2O—$, $CF_3O—$, $CF_3CH_2O—$ or $CH_3CF_2O—$ groups.

As used herein, the term "hydroxyl" or "hydroxy" means a —OH group.

As used herein, the term "cyano" means a —CN group.

As used herein, the term "halogen" refers to fluorine (fluoro), chlorine (chloro), bromine (bromo) or iodine (iodo).

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The terms "$C_1$-$C_{12}$alkyl" and "$C_1$-$C_4$alkyl" are to be construed accordingly. Examples of $C_1$-$C_6$alkyl include, but are not limited to, methyl, ethyl, n-propyl, n-butyl, n-pentyl, n-hexyl and the isomers thereof, for example, iso-propyl, iso-butyl, sec-butyl, tert-butyl or iso-amyl. A "$C_1$-$C_6$alkylene" group refers to the corresponding definition of $C_1$-$C_6$alkyl, except that such radical is attached to the rest of the molecule by two single bonds. The term "$C_1$-$C_2$alkylene" is to be construed accordingly. Examples of $C_1$-$C_6$alkylene, include, but are not limited to, —$CH_2$—, —$CH_2CH_2$— and —$(CH_2)_3$—.

As used herein, the term "$C_3$-$C_8$cycloalkyl" refers to a radical which is a monocyclic saturated ring system and which contains 3 to 8 carbon atoms. The term "$C_3$-$C_6$cycloalkyl" is to be construed accordingly. Examples of $C_3$-$C_8$cycloalkyl include, but are not limited to, cyclopropyl, cyclobutyl, cyclopentyl, cyclohexyl, cycloheptyl and cyclooctyl.

As used herein, the term "$C_3$-$C_8$halocycloalkyl" refers to a $C_3$-$C_8$cycloalkyl radical as generally defined above substituted by one or more of the same or different halogen atoms. The term "$C_3$-$C_6$halocycloalkyl" is to be construed accordingly.

As used herein, the term "$C_1$-$C_6$alkoxy" refers to a radical of the formula —$OR_a$ where $R_a$ is a $C_1$-$C_6$alkyl radical as generally defined above. The term "$C_1$-$C_4$alkoxy" is to be construed accordingly. Examples of $C_1$-$C_6$alkoxy include, but are not limited to, methoxy, ethoxy, 1-methylethoxy (iso-propoxy), propoxy, butoxy, 1-methylpropoxy and 2-methylpropoxy.

As used herein, the term "$C_1$-$C_6$haloalkyl" refers a $C_1$-$C_6$alkyl radical as generally defined above substituted by one or more of the same or different halogen atoms. The terms "$C_1$-$C_4$haloalkyl" and "$C_1$-$C_2$haloalkyl" are to be construed accordingly. Examples of $C_1$-$C_6$haloalkyl include, but are not limited to trifluoromethyl.

As used herein, the term "$C_1$-$C_6$alkoxy$C_1$-$C_6$alkoxy" refers to a radical of the formula $R_bO$—$R_aO$— where $R_b$ is a $C_1$-$C_6$alkyl radical as generally defined above, and $R_a$ is a $C_1$-$C_6$alkylene radical as generally defined above. Examples of $C_1$-$C_6$alkoxy$C_1$-$C_6$alkoxy include, but are not limited to, methoxymethoxy, ethoxymethoxy and methoxyethoxy.

As used herein, the term "$C_1$-$C_6$haloalkoxy$C_1$-$C_6$alkoxy" refers to a radical of the formula $R_bO$—$R_aO$—, where $R_a$ is a $C_1$-$C_6$alkylene radical as generally defined above and $R_b$ is a $C_1$-$C_6$alkyl radical as generally defined above substituted by one or more of the same or different halogen atoms. Examples of $C_1$-$C_6$haloalkoxy$C_1$-$C_6$alkoxy groups include, but not limited to trifluoromethoxymethoxy.

As used herein, the term "$C_1$-$C_6$alkoxy$C_1$-$C_6$haloalkoxy" refers to a radical of the formula $R_aO$—$R_bO$—, where $R_a$ is a $C_1$-$C_6$alkyl radical as generally defined above and $R_b$ is a $C_1$-$C_6$alkylene radical as generally defined above substituted by one or more of the same or different halogen atoms. Examples of $C_1$-$C_6$alkoxy$C_1$-$C_6$haloalkoxy groups include, but not limited to methoxydifluoromethoxy.

As used herein, the term "$C_2$-$C_6$acyl" refers to a radical $R_aC$(═O)—, where $R_a$ is a $C_1$-$C_5$alkyl radical as generally defined above. Acyl groups include, but are not limited to, acetyl and propanoyl.

As used herein, the term "$C_2$-$C_6$acyloxy" refers to a radical of the formula —$OR_a$ where $R_a$ is a $C_2$-$C_6$acyl as generally defined above. $C_2$-$C_6$acyloxy groups include, but are not limited to, acetoxy, propanoyloxy, isopropanoyloxy, butanoyloxy, and cyclopropanoyloxy.

As used herein, the term "$C_2$-$C_6$haloacyloxy" refers to a radical of the formula $R_aC$(═O)O—, where $R_a$ is $C_1$-$C_5$alkyl radical as generally defined above substituted by one or more of the same or different halogen atoms. $C_2$-$C_6$haloacyloxy groups include, but are not limited to trifluoroacetoxy.

As used herein, the term "$C_2$-$C_6$acyloxy$C_1$-$C_6$alkoxy" refers to a radical of the formula $R_aC$(═O)$OR_bO$— where $R_a$ is a $C_1$-$C_5$alkyl radical as generally defined above and where $R_b$ is a $C_1$-$C_6$alkylene radical as generally defined above.

As used herein, the term "$C_2$-$C_6$haloacyloxy$C_1$-$C_6$alkoxy" refers to a radical of the formula $R_aC$(═O)$OR_bO$— where $R_a$ is a $C_1$-$C_5$alkyl radical as generally defined above substituted by one or more of the same or different halogen atoms, and $R_b$ is a $C_1$-$C_6$alkylene radical as generally defined above.

As used herein, the term "$C_2$-$C_6$acyloxy$C_1$-$C_6$haloalkoxy" refers to a radical of the formula $R_aC$(═O)$OR_bO$— where $R_a$ is a $C_1$-$C_5$alkyl radical as generally defined above, and $R_b$ is a $C_1$-$C_6$alkylene radical as generally defined above substituted by one or more of the same or different halogen atoms.

As used herein, the term "heteroaryl" refers to a 5- or 6-membered aromatic monocyclic ring radical which comprises 1, 2, 3 or 4 heteroatoms individually selected from N, O and S. Examples of heteroaryl include, but are not limited to, furanyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryloxy" refers to a radical of the formula —$OR_a$ where $R_a$ is a heteroaryl radical as generally defined above. Examples of heteroaryloxy include, but are not limited to, pyridyloxy and thienyloxy.

As used herein, the term "heterodiaryl" refers to a 9- or 10-membered bicyclic aromatic system which comprises 1, 2, 3 or 4 heteroatoms individually selected from N, O and S. Examples of heterodiaryl include, but are not limited to quinolinyl and indolinyl.

As used herein, the term "heterodiaryloxy" refers to a radical of the formula —$OR_a$ where $R_a$ is a heterodiaryl radical as generally defined above.

The presence of one or more possible asymmetric carbon atoms in a compound of formula (I) means that the compounds may occur in optically isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as an N-oxide, or in salt form, e.g., an agronomically usable salt form.

N-oxides are oxidized forms of tertiary amines or oxidized forms of nitrogen-containing heteroaromatic compounds. They are described for instance in the book "Heterocyclic N-oxides" by A. Albini and S. Pietra, CRC Press, Boca Raton (1991).

The following list provides definitions, including preferred definitions, for substituents $R^1$, $R^2$, $R^3$, $R^4$, $R^5$, $R^6$, $R^7$, $R^8$, $R^9$ and $R^{10}$, with reference to compounds of formula (I). For any one of these substituents, any of the definitions given below may be combined with any definition of any other substituent given below or elsewhere in this document.

$R^1$ is $C_1$-$C_{12}$alkyl or $C_1$-$C_6$haloalkyl. Preferably, $R^1$ is $C_1$-$C_6$alkyl or $C_1$-$C_4$haloalkyl, more preferably, $C_1$-$C_4$alkyl or $C_1$-$C_2$haloalkyl, and even more preferably, $C_1$-$C_3$alkyl (including methyl or ethyl), difluoromethyl or trifluoromethyl. Particularly preferably, $R^1$ is methyl or ethyl, and in particular methyl.

$R^2$ is hydroxy, $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy or $C_2$-$C_6$acyloxy$C_1$-$C_6$haloalkoxy. Preferably, $R^2$ is hydroxy, $C_2$-$C_4$acyloxy, $C_2$-$C_4$haloacyloxy, $C_1$-$C_4$alkoxy$C_1$-$C_4$alkoxy, $C_1$-$C_4$haloalkoxy$C_1$-$C_4$alkoxy, $C_1$-$C_4$alkoxy$C_1$-$C_4$haloalkoxy, $C_2$-$C_4$acyloxy$C_1$-$C_4$alkoxy, $C_2$-$C_4$haloacyloxy$C_1$-$C_4$alkoxy or $C_2$-$C_4$acyloxy$C_1$-$C_4$haloalkoxy. More preferably, $R^2$ is hydroxy, acetoxy, propanoyloxy, acetoxymethoxy, propanoyloxymethoxy, 2-methyl-propanoyloxymethoxy. Particularly preferably, $R^2$ is hydroxy.

$R^3$ is hydrogen, $C_1$-$C_6$alkyl, $C_1$-$C_6$alkoxy or $C_3$-$C_8$cycloalkyl. Preferably, $R^3$ is hydrogen, $C_1$-$C_4$alkyl, $C_1$-$C_4$alkoxy or $C_3$-$C_6$cycloalkyl, and more preferably, hydrogen, methyl, ethyl, methoxy, cyclopropyl. More preferably, $R^3$ is hydrogen.

$R^4$ and $R^5$ are independently selected from $C_1$-$C_{12}$alkyl, $C_3$-$C_8$cycloalkyl, $C_1$-$C_6$haloalkyl, $C_1$-$C_6$alkoxy$C_1$-$C_6$alkyl and $C_3$-$C_8$halocycloalkyl. Preferably, $R^4$ and $R^5$ are independently selected from $C_1$-$C_4$alkyl, $C_3$-$C_6$cycloalkyl, $C_1$-$C_4$haloalkyl, $C_1$-$C_4$alkoxy$C_1$-$C_4$alkyl and $C_3$-$C_6$halocycloalkyl. More preferably, $R^4$ and $R^5$ are independently selected from methyl, ethyl, cyclopropyl, difluoromethyl, trifluoromethyl, methoxymethyl, ethoxymethyl, ethoxymethyl and fluorocyclopropyl. Even more preferably, $R^4$ is methyl or ethyl and $R^5$ is methyl or ethyl (including $R^4$ is methyl and $R^5$ is ethyl, or $R^4$ is ethyl and $R^5$ is methyl), and in particular, $R^4$ and $R^5$ are methyl.

$R^6$ and $R^7$ are independently selected from $C_1$-$C_6$alkyl or $C_3$-$C_8$cycloalkyl. Preferably, $R^6$ and $R^7$ are independently selected from $C_1$-$C_4$alkyl or $C_3$-$C_6$cycloalkyl. More preferably, $R^6$ and $R^7$ are independently selected from methyl, ethyl or cyclopropyl. More preferably, $R^6$ and $R^7$ are methyl.

Otherwise, $R^6$ and $R^7$ together with the carbon atom to which they are attached may form a $C_3$-$C_8$cycloalkyl ring, preferably a $C_3$-$C_6$cycloalkyl ring (i.e., cyclopropyl, cyclobutyl, cyclopentyl or cyclohexyl), and more preferably a cyclopropyl ring, which is optionally substituted by 1, 2 or 3 substituents, which may be the same or different, selected from $R^9$, or is optionally substituted by a single substituent which is $R^{10}$, or is optionally substituted by 1 or 2 substituents, which may be the same or different, selected from $R^9$ and a single substituent which is $R^{10}$.

$R^8$ is phenyl, phenoxy, naphthyl, naphthyloxy, heteroaryl or heteroaryloxy, wherein the heteroaryl moiety is a 5- or 6-membered aromatic ring which comprises 1, 2, 3 or 4 heteroatoms individually selected from N, O and S, heterodiaryl or heterodiaryloxy, wherein the heterodiaryl moiety is a 9- or 10-membered bicyclic aromatic system which comprises 1, 2, 3 or 4 heteroatoms individually selected from N, O and S, wherein each phenyl, naphthyl, heteroaryl or heterodiaryl is optionally substituted by 1, 2 or 3 substituents, which may be the same or different, selected from $R^9$.

Preferably, $R^8$ is phenyl, naphthyl, furyl, benzofuryl, thienyl, benzothienyl, pyrrolyl, indolyl, pyrazolyl, indazolyl, imidazolyl, benzimidazolyl, thiazolyl, benzothiazolyl, oxazolyl, benzoxazolyl, pyridyl, quinolinyl, isoquinolinyl, pyridazinyl, cinnolinyl, pyrimidinyl, quinazolinyl, pyrazinyl, phenoxy, naphthyloxy, pyridyloxy or quinolinyloxy. More preferably, $R^8$ is phenyl, naphthyl, thienyl, indolyl, pyridyl, quinolinyl, pyridazinyl, pyrimidinyl, pyrazinyl, phenoxy, pyridyloxy or quinolinyloxy. Still more preferably, $R^8$ is phenyl, naphthyl (1-naphthyl, 2-naphthyl), thienyl (2-thienyl, 3-thienyl), pyridyl (2-pyridyl, 3-pyridyl, 4-pyridyl), quinolinyl (including 2-quinolinyl, 3-quinolinyl), phenoxy or pyridyloxy (including 2-pyridyloxy, 3-pyridyloxy). Even more preferably, $R^8$ is phenyl, thienyl (2-thienyl, 3-thienyl), pyridyl (2-pyridyl, 3-pyridyl, 4-pyridyl), phenoxy or pyridyloxy (2-pyridyloxy, 3-pyridyloxy), and in particular phenyl.

For $R^8$, heteroaryl and heterodiaryl substituents may be bound to the rest of the molecule by a carbon atom or a heteroatom.

When $R^8$ is substituted, it may be substituted by 1 or 2 substituents, which may be the same or different, selected from $R^9$. Otherwise, when $R^8$ is substituted, it may be substituted by a single substituent selected from $R^9$.

$R^9$ is halogen, cyano, $C_1$-$C_4$alkyl, $C_1$-$C_4$haloalkyl, $C_1$-$C_4$alkoxy, $C_1$-$C_4$haloalkoxy. Preferably, $R^9$ is fluoro, chloro, bromo, cyano, methyl, ethyl, difluoromethyl, trifluoromethyl, methoxy, ethoxy or trifluoromethoxy. More preferably, $R^9$ is fluoro, chloro, cyano, methyl, ethyl, difluoromethyl, trifluoromethyl, methoxy, ethoxy or trifluoromethoxy. In one set of embodiments, $R^9$ is fluoro, chloro, bromo, trifluoromethyl, ethoxy or trifluoromethoxy.

$R^{10}$ is phenyl or cyclopropyl each optionally substituted by 1, 2 or 3 substituents, which may be the same or different, selected from fluoro, chloro, bromo, cyano, methyl, ethyl, difluoromethyl, trifluoromethyl, methoxy, ethoxy, difluoromethoxy, trifluoromethoxy. When $R^{10}$ is substituted, it may be substituted by 1 or 2 substituents, which may be the same or different. Otherwise, when $R^{10}$ is substituted, it may be substituted by a single substituent, preferably fluoro.

In a compound of formula (I) according to the present invention, preferably:

$R^1$ is methyl or ethyl;

$R^2$ is hydroxy, acetoxy, propanoyloxy, acetoxymethoxy, propanoyloxymethoxy or 2-methyl-propanoyloxymethoxy;

$R^3$ is hydrogen, methyl, ethyl, methoxy or cyclopropyl;

$R^4$ is methyl or ethyl and $R^5$ is methyl or ethyl;

$R^6$ and $R^7$ are independently selected from methyl, ethyl or cyclopropyl, or $R^6$ and $R^7$ together with the carbon atom to which they are attached form a $C_3$-$C_6$cycloalkyl ring which is optionally substituted by by 1 or 2 substituents, which may be the same or different, selected from $R^9$, or is optionally substituted by a single substituent which is $R^{10}$;

$R^8$ is phenyl, naphthyl, thienyl, indolyl, pyridyl, quinolinyl, pyridazinyl, pyrimidinyl, pyrazinyl, phenoxy, pyridyloxy or quinolinyloxy optionally substituted by 1 or 2 substituents, which may be the same or different, selected from $R^9$;

$R^9$ is fluoro, chloro, cyano, methyl, ethyl, difluoromethyl, trifluoromethyl, methoxy, ethoxy or trifluoromethoxy;

$R^{10}$ is phenyl or cyclopropyl each optionally substituted by 1 or 2 substituents, which may be the same or different, selected from fluoro, chloro, bromo, cyano, methyl, ethyl, difluoromethyl, trifluoromethyl, methoxy, ethoxy, difluoromethoxy, trifluoromethoxy.

More preferably, $R^1$ is methyl or ethyl;

$R^2$ is hydroxy;

$R^3$ is hydrogen;

$R^4$ is methyl or ethyl and $R^5$ is methyl or ethyl;

$R^6$ and $R^7$ are independently selected from methyl, ethyl or cyclopropyl, or $R^6$ and $R^7$ together with the carbon atom to which they are attached form a $C_3$-$C_6$cycloalkyl ring which is optionally substituted by by 1 or 2 substituents, which may be the same or different, selected from $R^9$, or is optionally substituted by a single substituent which is $R^{10}$;

$R^8$ is phenyl, naphthyl, thienyl, indolyl, pyridyl, quinolinyl, pyridazinyl, pyrimidinyl, pyrazinyl, phenoxy, pyridyloxy or quinolinyloxy optionally substituted by 1 or 2 substituents, which may be the same or different, selected from $R^9$;

$R^9$ is fluoro, chloro, cyano, methyl, ethyl, difluoromethyl, trifluoromethyl, methoxy, ethoxy or trifluoromethoxy;

$R^{10}$ is phenyl or cyclopropyl each optionally substituted by 1 or 2 substituents, which may be the same or different, selected from fluoro, chloro, bromo, cyano, methyl, ethyl, difluoromethyl, trifluoromethyl, methoxy, ethoxy, difluoromethoxy, trifluoromethoxy.

Even more preferably, $R^1$ is methyl;

$R^2$ is hydroxy;

$R^3$ is hydrogen;

$R^4$ and $R^5$ are methyl;

$R^6$ and $R^7$ are methyl, or $R^6$ and $R^7$ together with the carbon atom to which they are attached form a $C_3$-$C_6$cycloalkyl ring which is optionally substituted by by 1 or 2 substituents, which may be the same or different, selected from $R^9$, or is optionally substituted by a single substituent which is $R^{10}$;

$R^8$ is phenyl, thienyl, pyridyl, phenoxy or pyridyloxy optionally substituted by 1 or 2 substituents, which may be the same or different, selected from $R^9$;

$R^9$ is fluoro, chloro, cyano, methyl, ethyl, difluoromethyl, trifluoromethyl, methoxy, ethoxy or trifluoromethoxy;

$R^{10}$ is phenyl or cyclopropyl each optionally substituted by 1 or 2 substituents, which may be the same or different, selected from fluoro, chloro, bromo, cyano, methyl, ethyl, difluoromethyl, trifluoromethyl, methoxy, ethoxy, difluoromethoxy, trifluoromethoxy.

Still more preferably, $R^1$ is methyl;

$R^2$ is hydroxy;

$R^3$ is hydrogen;

$R^4$ and $R^5$ are methyl;

$R^6$ and $R^7$ are methyl, or $R^6$ and $R^7$ together with the carbon atom to which they are attached form a cyclopropyl ring which is optionally substituted by 1 or 2 substituents, which may be the same or different, selected from $R^9$, or is optionally substituted by a single substituent which is $R^{10}$;

$R^8$ is phenyl optionally substituted by 1 or 2 substituents, which may be the same or different, selected from $R^9$;

$R^9$ is fluoro, chloro, cyano, methyl, ethyl, difluoromethyl, trifluoromethyl, methoxy, ethoxy or trifluoromethoxy;

$R^{10}$ is phenyl or cyclopropyl each optionally substituted by 1 or 2 substituents, which may be the same or different, selected from fluoro, chloro, bromo, cyano, methyl, ethyl, difluoromethyl, trifluoromethyl, methoxy, ethoxy, difluoromethoxy, trifluoromethoxy.

In a particular set of embodiments according to the invention, $R^1$ is methyl;

$R^2$ is hydroxy or acetoxy;

$R^3$ is hydrogen;

$R^4$ and $R^5$ are methyl;

$R^6$ and $R^7$ are methyl, or $R^6$ and $R^7$ together with the carbon atom to which they are attached form a cyclopropyl ring which is optionally substituted by 1 or 2 substituents, which may be the same or different, selected from $R^9$, or is optionally substituted by a single substituent which is $R^{10}$; or $R^6$ and $R^7$ together with the carbon atom to which they are attached form a cyclobutyl, cyclopentyl or cyclohexyl ring;

$R^8$ is naphthyl, or $R^8$ is phenyl optionally substituted by 1 or 2 substituents, which may be the same or different, selected from $R^9$;

$R^9$ is fluoro, chloro, bromo, trifluoromethyl, ethoxy or trifluoromethoxy; and $R^{10}$ is phenyl or 4-fluorophenyl.

Preferably, the compound according to formula (I) is a compound described in Table 2 (below) and/or is one of the following preferred compounds.

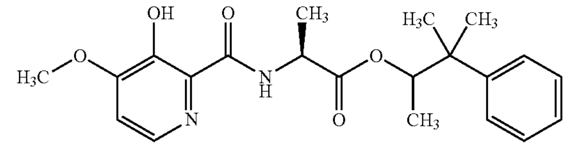

(1,2-dimethyl-2-phenyl-propyl)(2S)-2-[(3-hydroxy-4-methoxy-pyridine-2-carbonyl)amino]propanoate

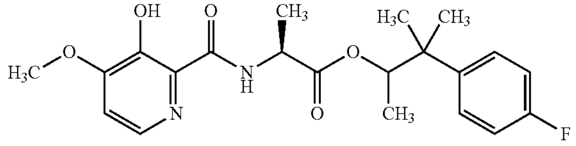

[2-(4-fluorophenyl)-1,2-dimethyl-propyl](2S)-2-[(3-hydroxy-4-methoxy-pyridine-2-carbonyl)amino]propanoate

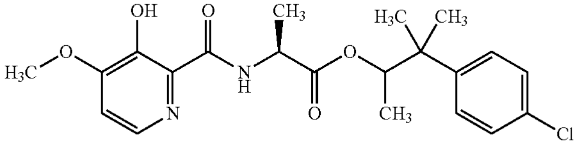

[2-(4-chlorophenyl)-1,2-dimethyl-propyl](2S)-2-[(3-hydroxy-4-methoxy-pyridine-2-carbonyl)amino]propanoate

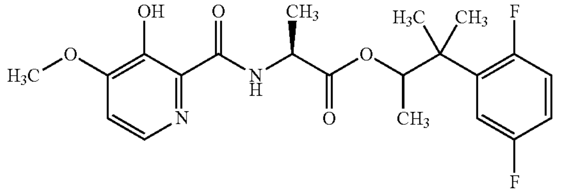

[2-(2,5-difluorophenyl)-1,2-dimethyl-propyl](2S)-2-[(3-hydroxy-4-methoxy-pyridine-2-carbonyl)amino]propanoate

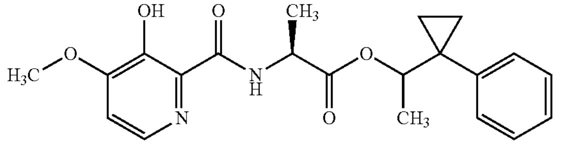

1-(1-phenylcyclopropyl)ethyl(2S)-2-[(3-hydroxy-4-methoxy-pyridine-2-carbonyl)amino]propanoate

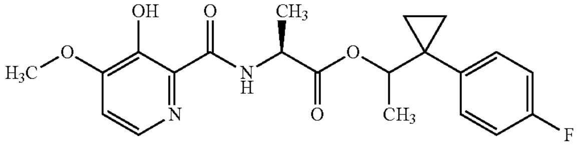

1-[1-(4-fluorophenyl)cyclopropyl]ethyl(2S)-2-[(3-hydroxy-4-methoxy-pyridine-2-carbonyl)amino]propanoate

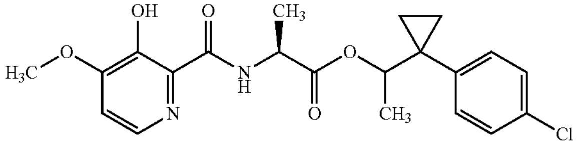

1-[1-(4-chlorophenyl)cyclopropyl]ethyl(2S)-2-[(3-hydroxy-4-methoxy-pyridine-2-carbonyl)amino]propanoate -continued

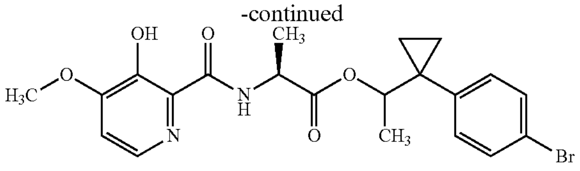

1-[1-(4-bromophenyl)cyclopropyl]ethyl(2S)-2-[(3-hydroxy-4-methoxy-pyridine-2-carbonyl)amino]propanoate

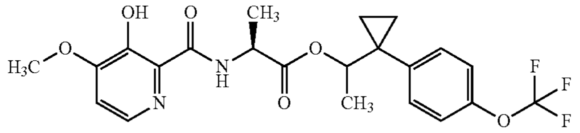

1-[1-[4-(trifluoromethoxy)phenyl]cyclopropyl]ethyl(2S)-2-[(3-hydroxy-4-methoxy-pyridine-2-carbonyl)amino]propanoate

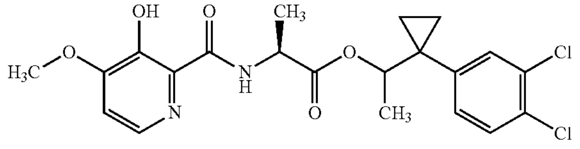

1-[1-(3,4-dichlorophenyl)cyclopropyl]ethyl(2S)-2-[(3-hydroxy-4-methoxy-pyridine-2-carbonyl)amino]propanoate

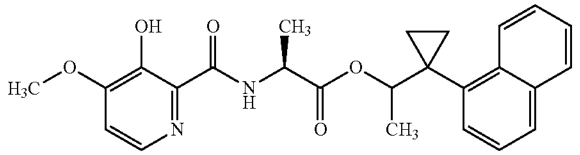

1-[1-(1-naphthyl)cyclopropyl]ethyl(2S)-2-[(3-hydroxy-4-methoxy-pyridine-2-carbonyl)amino]propanoate

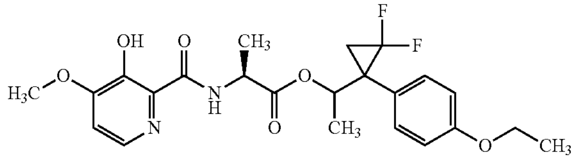

1-[1-(4-ethoxyphenyl)-2,2-difluoro-cyclopropyl]ethyl(2S)-2-[(3-hydroxy-4-methoxy-pyridine-2-carbonyl)amino]propanoate

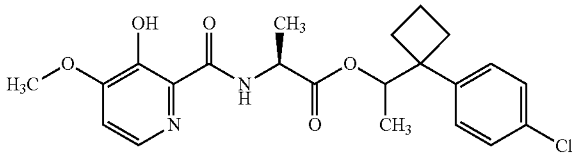

1-[1-(4-chlorophenyl)cyclobutyl]ethyl(2S)-2-[(3-hydroxy-4-methoxy-pyridine-2-carbonyl)amino]propanoate

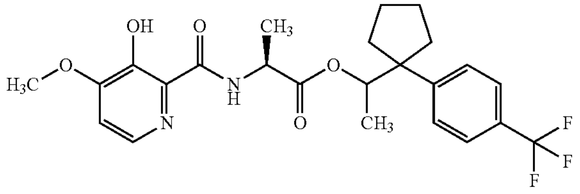

1-[1-[4-(trifluoromethyl)phenyl]cyclopentyl]ethyl(2S)-2-[(3-hydroxy-4-methoxy-pyridine-2-carbonyl)amino]propanoate -continued

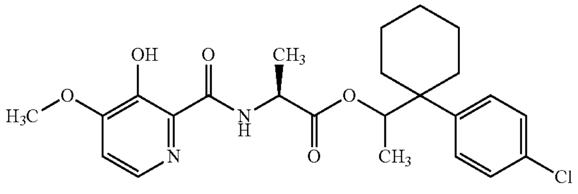

1-[1-(4-chlorophenyl)cyclohexyl]ethyl(2S)-2-[(3-hydroxy-4-methoxy-pyridine-2-carbonyl)amino]propanoate

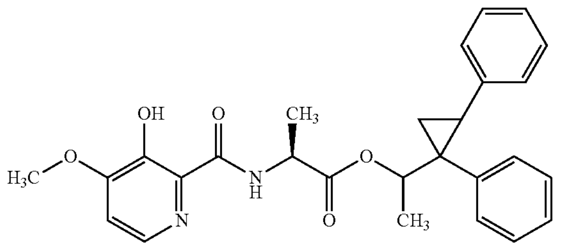

1-(1,2-diphenylcyclopropyl)ethyl(2S)-2-[(3-hydroxy-4-methoxy-pyridine-2-carbonyl)amino]propanoate

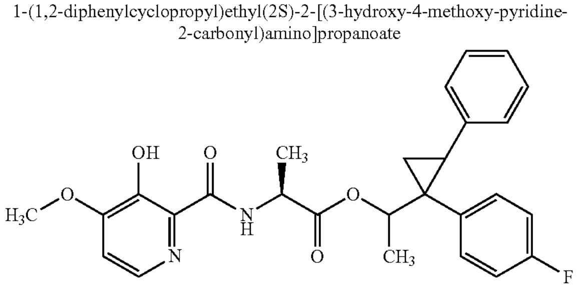

1-[1-(4-fluorophenyl)-2-phenyl-cyclopropyl]ethyl(2S)-2-[(3-hydroxy-4-methoxy-pyridine-2-carbonyl)amino]propanoate

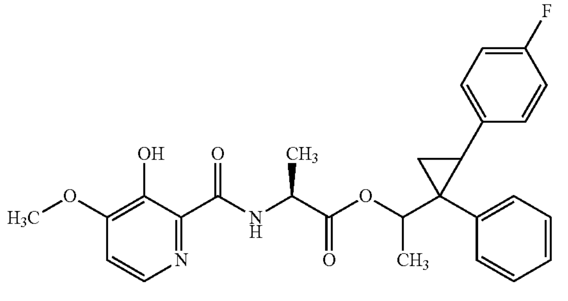

1-[2-(4-fluorophenyl)-1-phenyl-cyclopropyl]ethyl(2S)-2-[(3-hydroxy-4-methoxy-pyridine-2-carbonyl)amino]propanoate The compounds of Formula (I) according to the present invention may possess three chiral centres at carbon atoms A, B and C as outlined below in Formula (A).

(I)

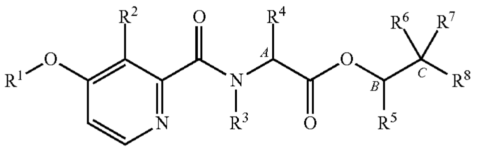

Accordingly, as already indicated, the compounds of Formula (I) may exist in various diastereomeric forms, ie, with (S,S,S)-, (S,S,R)-, (S,R,R)-, (S,R,S)-, (R,R,R)-, (R,R,S)-, (R,S,S)- or (R,S,R)-configurations present at the A, B and C carbons, respectively. In particular, each of these configurations may be evident for compounds of Formula (I) in relation to the specifc combinations of definitions for $R^1$, $R^2$, $R^3$, $R^4$, $R^5$, $R^6$, $R^7$ and $R^8$ for each compound described in Table 1 (a compound of Formulae (1.a) to (1.ah)) or a compound of Formula (I) described in Table 2 (below).

Compounds of the present invention can be made as shown in the following schemes, in which, unless otherwise stated, the definition of each variable is as defined above for a compound of formula (I).

The compounds of formula (I) according to the invention, wherein $R^1$, $R^2$, $R^3$, $R^4$, $R^5$, $R^6$, $R^7$ and $R^8$ are as defined for formula (I), can be obtained by transformation of a compound of formula (II), wherein $R^1$ and $R^2$ are as defined for formula (I) and $R^{11}$ is hydroxy or halogen, with a compound of formula (III), wherein $R^3$, $R^4$, $R^5$, $R^6$, $R^7$ and $R^8$ are as defined for formula (I), and with a base or a peptide coupling reagent. This is shown in Scheme 1 below.

Scheme 1

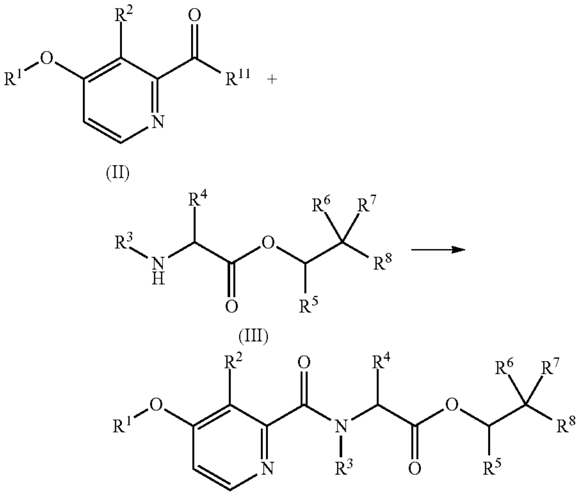

(II)

(III)

(I)

Alternatively, the compounds of formula (I), wherein $R^1$, $R^2$, $R^3$, $R^4$, $R^5$, $R^6$, $R^7$ and $R^8$ are as defined for formula (I), can be obtained by transformation of a compound of formula (IV), wherein $R^1$, $R^2$, $R^3$, and $R^4$ are as defined for formula (I) and $R^{11}$ is hydroxy or halogen, with a compound of formula (V), wherein $R^5$, $R^6$, $R^7$ and $R^8$ are as defined for formula (I), and with an acid or a base. This is shown in Scheme 2 below.

Scheme 2

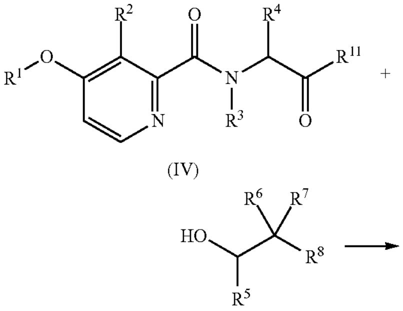

(IV)

(V)

-continued

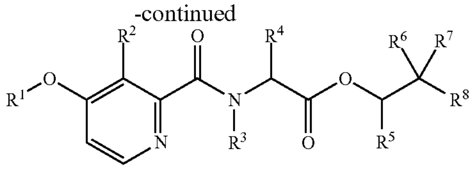

(I)

The compounds of formula (III), wherein $R^3$, $R^4$, $R^5$, $R^6$, $R^7$ and $R^8$ are as defined for formula (I), can be obtained by transformation of a compound of formula (VI), wherein $R^3$, $R^4$, $R^5$, $R^6$, $R^7$ and $R^8$ are as defined for formula (I) and $R^{12}$ is $C_1$-$C_6$alkylcarbonyl or $C_1$-$C_6$alkoxycarbonyl, and with an acid. This is shown in Scheme 3 below.

Scheme 3

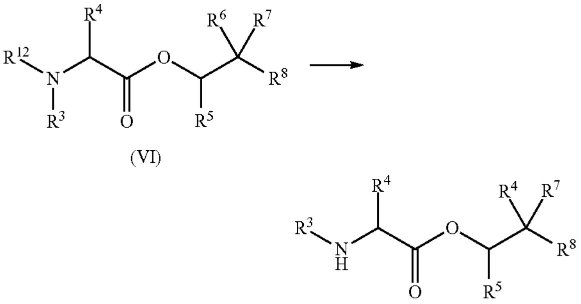

(VI)

(III)

The compounds of formula (VI), wherein $R^3$, $R^4$, $R^5$, $R^6$, $R^7$ and $R^8$ are as defined for formula (I) and $R^{12}$ is $C_1$-$C_6$alkylcarbonyl or $C_1$-$C_6$alkoxycarbonyl, can be obtained by transformation of a compound of formula (VII), wherein $R^3$ and $R^4$ are as defined for formula (I), $R^{11}$ is hydroxy or halogen and $R^{12}$ is $C_1$-$C_6$alkylcarbonyl or $C_1$-$C_6$alkoxycarbonyl, with a compound of formula (V), wherein $R^5$, $R^6$, $R^7$ and $R^8$ are as defined for formula (I), and with an acid or a base. This is shown in Scheme 4 below.

Scheme 4

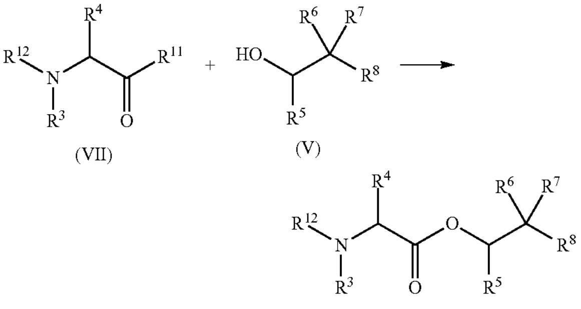

(VII)

(V)

(VI)

The compounds of formula (IV), wherein $R^1$, $R^2$, $R^3$, and $R^4$ are as defined for formula (I) and $R^{11}$ is hydroxy or halogen, can be obtained by transformation of a compound of formula (VIII), wherein $R^1$, $R^2$, $R^3$, and $R^4$ are as defined for formula (I) and $R^{13}$ is $C_1$-$C_6$alkyl, and with a base or a halogenation agent. This is shown in Scheme 5 below.

Scheme 5

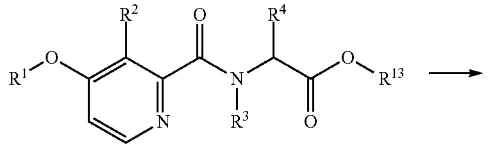

(VIII)

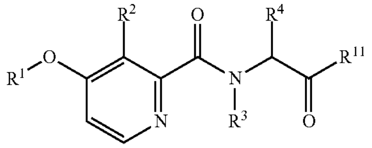

(IV)

The compounds of formula (VIII), wherein $R^1$, $R^2$, $R^3$, and $R^4$ are as defined for formula (I) and $R^{13}$ is $C_1$-$C_6$alkyl, can be obtained by transformation of a compound of formula (II), wherein $R^1$ and $R^2$ are as defined for formula (I) and $R^{11}$ is hydroxy or halogen, with a compound of formula (IX), wherein $R^3$ and $R^4$ are as defined for formula (I) and $R^{13}$ is $C_1$-$C_6$alkyl, and with a base or a peptide coupling reagent. This is shown in Scheme 6 below.

Scheme 6

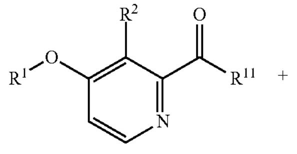

(II)

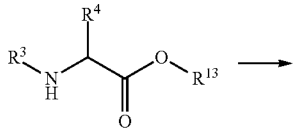

(IX)

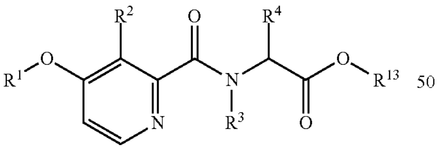

(VIII)

The compounds of formula (I-B), wherein $R^1$, $R^3$, $R^4$, $R^5$, $R^6$, $R^7$ and R are as defined for formula (I) and $R^{14}$ is $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy, can be obtained by transformation of a compound of formula (I-A), wherein $R^1$, $R^3$, $R^4$, $R^5$, $R^6$, $R^7$ and $R^8$ are as defined for formula (I), with a compound of formula (X), wherein $R^{14}$ is $C_2$-$C_6$acyloxy, $C_2$-$C_6$haloacyloxy, $C_1$-$C_6$alkoxy$C_1$-$C_6$alkoxy, $C_2$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy and $R^{15}$ is halogen, and with a base. This is shown in Scheme 7 below.

Scheme 7

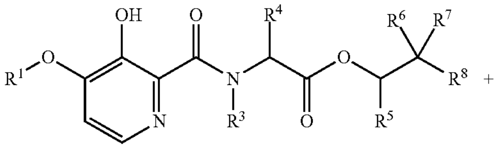

(I-A)

$R^{14}$—$R^{15}$ (X)

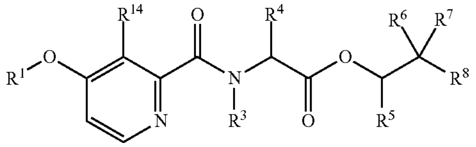

(I-B)

The compounds of formula (I-A), wherein $R^1$, $R^3$, $R^4$, $R^5$, $R^6$, $R^7$ and R are as defined for formula (I), can be obtained by transformation of a compound of formula (II-A), wherein $R^1$ is as defined for formula (I) and $R^{11}$ is hydroxy or halogen, with a compound of formula (III), wherein $R^3$, $R^4$, $R^5$, $R^6$, $R^7$ and $R^8$ are as defined for formula (I), and with a base or a peptide coupling reagent. This is shown in Scheme 8 below.

Scheme 8

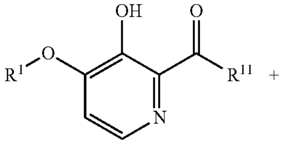

(II-A)

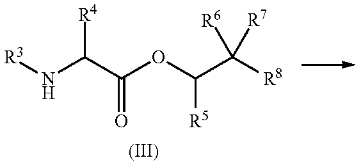

(III)

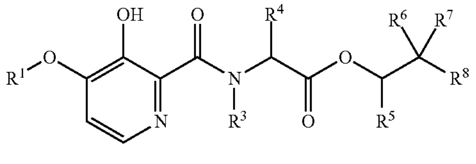

(I-A)

Alternatively, the compounds of formula (I-A), wherein $R^1$, $R^3$, $R^4$, $R^5$, $R^6$, $R^7$ and $R^8$ are as defined for formula (I), can be obtained by transformation of a compound of formula (IV-A), wherein $R^1$, $R^3$, and $R^4$ are as defined for formula (I) and $R^{11}$ is hydroxy or halogen, with a compound of formula (V), wherein $R^5$, $R^6$, $R^7$ and $R^8$ are as defined for formula (I), and with an acid or a base. This is shown in Scheme 9 below.

Scheme 9

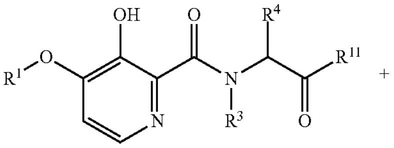

(IV-A)

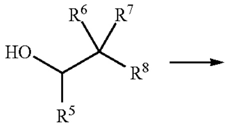

(V)

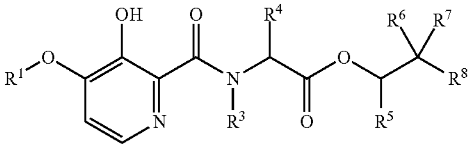

(I-A)

Alternatively, the compounds of formula (I-B) according to the invention, wherein $R^1$, $R^2$, $R^3$, $R^4$, $R^5$, $R^6$, $R^7$ and $R^8$ are as defined for formula (I) and $R^{14}$ is $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy, can be obtained by transformation of a compound of formula (IV-B), wherein $R^1$, $R^3$ and $R^4$ are as defined for formula (I), $R^{11}$ is hydroxy or halogen and $R^{14}$ is $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy, with a compound of formula (V), wherein $R^5$, $R^6$, $R^7$ and $R^8$ are as defined for formula (I), and with an acid or a base. This is shown in Scheme 10 below.

Scheme 10

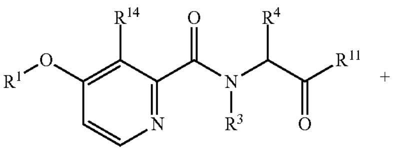

(IV-B)

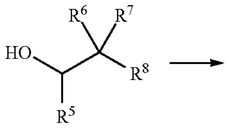

(V)

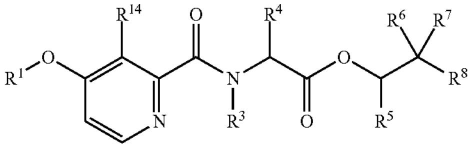

(I-B)

The compounds of formula (IV-B), wherein $R^1$, $R^3$ and $R^4$ are as defined for formula (I) $R^{11}$ is hydroxy or halogen and $R^{14}$ is $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy, can be obtained by transformation of a compound of formula (VIII-B), wherein $R^1$, $R^3$, and $R^4$ are as defined for formula (I), $R^{13}$ is $C_1$-$C_6$alkyl and $R^{14}$ is $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy, and with a base or a halogenation agent. This is shown in Scheme 11 below.

Scheme 11

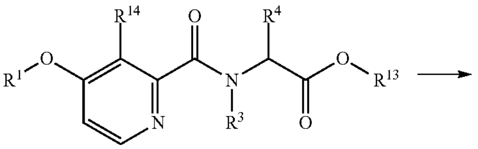

(VIII-B)

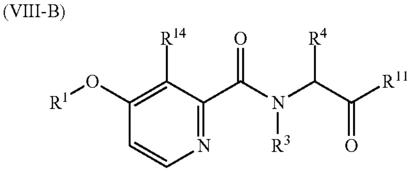

(IV-B)

The compounds of formula (VIII-B), wherein $R^1$, $R^3$, and $R^4$ are as defined for formula (I), $R^{13}$ is $C_1$-$C_6$alkyl and $R^{14}$ is $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy, can be obtained by transformation of a compound of formula (VIII-A), wherein $R^1$, $R^3$, and $R^4$ are as defined for formula (I) and $R^{13}$ is $C_1$-$C_6$alkyl, with a compound of formula (X), wherein $R^{14}$ is $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy, or $C_2$-$C_6$acyloxy$C_1$-$C_6$haloalkoxy and $R^{15}$ is halogen, and with a base. This is shown in Scheme 12 below.

Scheme 12

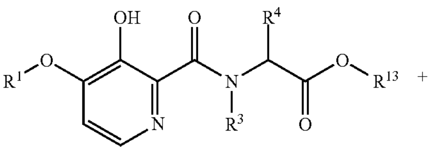

(VIII-A)

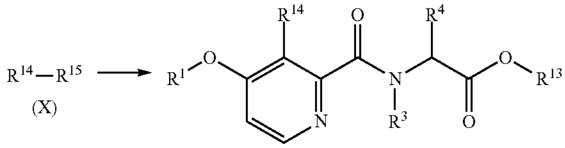

(X)

(VIII-B)

Surprisingly, it has now been found that the novel compounds of formula (I) have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use the compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seeds, such as fruits, tubers or grains, or plant cuttings (e.g., rice), for the protection against fungal infections, as well as against phytopathogenic fungi occurring in the soil. The propagation material can be treated with a composition comprising a compound of formula (I) before planting: seeds, e.g., can be dressed before being sown.

The active ingredients according to the invention can also be applied to grains (coating), either by impregnating the seeds in a liquid formulation or by coating them with a solid formulation. The composition can also be applied to the planting site when the propagation material is being planted, e.g., to the seed furrow during sowing. The invention relates also to such methods of treating plant propagation material and to the plant propagation material so treated.

Furthermore, the compounds according to the present invention can be used for controlling fungi in related areas, for example in the protection of technical materials, including wood and wood related technical products, in food storage, in hygiene management.

In addition, the invention could be used to protect nonliving materials from fungal attack, e.g., lumber, wall boards and paint.

The compounds of formula (I) may be, for example, effective against fungi and fungal vectors of disease as well as phytopathogenic bacteria and viruses. These fungi and fungal vectors of disease as well as phytopathogenic bacteria and viruses are for example: *Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. including *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca* (*Sphaerotheca fuliginea*), *Sporothorix* spp, *Stagonospora nodorum, Stemphylium* spp., *Stereum hirsutum, Thanatephorus cucumeris, Thielaviopsis basicola, Tilletia* spp, *Trichoderma* spp., including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens*, *Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The compounds of Formula (I) according to the present invention (including any one of compounds described in Table 2 (below)) may be used in controlling or preventing phytopathogenic diseases, especially phytopathogenic fungi (such as *Phakopsora pachyrhizi*) on soy bean plants.

In particular, transgenic soybean plants expressing toxins, for example insecticidal proteins such as delta-endotoxins, e.g. Cry1Ac (Cry1Ac Bt protein). Accordingly, this may include transgenic soybean plants comprising event MON87701 (see U.S. Pat. No. 8,049,071 and related applications and patents, as well as WO 2014/170327 A1 (eg, see paragraph [008] reference to Intacta RR2 PRO™ soybean)), event MON87751 (US. Patent Application Publication No. 2014/0373191) or event DAS-81419 (U.S. Pat. No. 8,632,978 and related applications and patents).

Other transgenic soybean plants may comprise event SYHTOH2—HPPD tolerance (U.S. Patent Application Publication No. 2014/0201860 and related applications and patents), event MON89788-glyphosate tolerance (U.S. Pat. No. 7,632,985 and related applications and patents), event MON87708—dicamba tolerance (U.S. Patent Application Publication No. US 2011/0067134 and related applications and patents), event DP-356043-5—glyphosate and ALS tolerance (U.S. Patent Application Publication No. US 2010/0184079 and related applications and patents), event A2704-12—glufosinate tolerance (U.S. Patent Application Publication No. US 2008/0320616 and related applications and patents), event DP-305423-1—ALS tolerance (U.S. Patent Application Publication No. US 2008/0312082 and related applications and patents), event A5547-127—glufosinate tolerance (U.S. Patent Application Publication No. US 2008/0196127 and related applications and patents), event DAS-40278-9—tolerance to 2,4-dichlorophenoxyacetic acid and aryloxyphenoxypropionate (see WO 2011/022469, WO 2011/022470, WO 2011/022471, and related applications and patents), event 127—ALS tolerance (WO 2010/080829 and related applications and patents), event GTS 40-3-2—glyphosate tolerance, event DAS-68416-4-2,4-dichlorophenoxyacetic acid and glufosinate tolerance, event FG72—glyphosate and isoxaflutole tolerance, event BPS-CV127-9—ALS tolerance and GU262—glufosinate tolerance or event SYHT04R—HPPD tolerance.

Under certain circumstances, compounds of Formula (I) according to the present invention when used in controlling or preventing phytopathogenic diseases, especially phytopathogenic fungi (such as *Phakopsora pachyrhizi*) on soy bean plants (in particular any of the transgenic soybean plants as described above), may display a synergistic interaction between the active ingredients.

Additionally, to date, no cross-resistance has been observed between the compounds of Formula (I) (including any one of compounds described in Table 2 (below)) and the current fungicidal solutions used to control *Phakopsora pachyrhizi.*

Indeed, fungicidal-resistant strains of *Phakopsora pachyrhizi* have been reported in the scientific literature, with strains resistant to one or more fungicides from at least each of the following fungicidal mode of action classes being observed: sterol demethylation-inhibitors (DMI), quinone-outside-inhibitors (QoI) and succinate dehydrogenase inhibitors (SDHI). See for example: "Sensitivity of *Phakopsora pachyrhizi* towards quinone-outside-inhibitors and demethylation-inhibitors, and corresponding resistance mechanisms." Schmitz H K et al, *Pest Manag Sci* (2014) 70: 378-388; "First detection of a SDH variant with reduced SDHI sensitivity in *Phakopsora pachyrhizi*" Simões K et al, *J Plant Dis Prot* (2018) 125: 21-2; "Competitive fitness of *Phakopsora pachyrhizi* isolates with mutations in the CYP51 and CYTB genes." Klosowski A C et al, *Phytopathology* (2016) 106: 1278-1284; "Detection of the F129L mutation in the cytochrome b gene in *Phakopsora pachyrhizi*." Klosowski A C et al, *Pest Manag Sci* (2016) 72: 1211-1215.

Thus, in a preferred embodiment, the compounds of Formula (I) (including any one of compounds described in Table 2 (below)), or fungicidal compositions according to the present invention comprising a compound of Formula (I), are used to control *Phakopsora pachyrhizi* which are resistant to one or more fungicides from any of the following fungicidal MoA classes: sterol demethylation-inhibitors (DMI), quinone-outside-inhibitors (QoI) and succinate dehydrogenase inhibitors (SDHI).

The compounds of Formula (I) (including any one of compounds described in Table 2 (below)) or fungicidal compositions according to the present invention comprising a compound of Formula (I) may be used in controlling or preventing phytopathogenic diseases, especially phytopathogenic fungi (such as *Phakopsora pachyrhizi*) on soy bean plants. In particular, there are known in the scientific literature certain Elite soybean plant varieties where R-gene stacks, conferring a degree of immunity or resistance to specific *Phakopsora pachyrhizi*, have been been introgressed in the plant genome, see for example: "*Fighting Asian Soybean Rust*", Langenbach C, et al, *Front Plant Science* 7(797) 2016).

An elite plant is any plant from an elite line, such that an elite plant is a representative plant from an elite variety. Non-limiting examples of elite soybean varieties that are commercially available to farmers or soybean breeders include: AG00802, A0868, AG0902, A1923, AG2403, A2824, A3704, A4324, A5404, AG5903, AG6202 AG0934; AG1435; AG2031; AG2035; AG2433; AG2733; AG2933; AG3334; AG3832; AG4135; AG4632; AG4934; AG5831; AG6534; and AG7231 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-K2 (NK Division of Syngenta Seeds, Golden Valley, Minn., USA); 90M01, 91M30, 92M33, 93M11, 94M30, 95M30, 97B52, P008T22R2; P16T17R2; P22T69R; P25T51R; P34T07R2; P35T58R; P39T67R; P47T36R; P46T21R; and P56T03R2 (Pioneer Hi-Bred International, Johnston, Iowa, USA); SG4771NRR and SG5161NRR/STS (Soygenetics, LLC, Lafayette, Ind., USA); S00-K5, S11-L2, S28-Y2, S43-B1, S53-A1, S76-L9, S78-G6, S0009-M2; S007-Y4; S04-D3; S14-A6; S20-T6; S21-M7; S26-P3; S28-N6; S30-V6; S35-$C_3$; S36-Y6; S39-$C_4$; S47-K5; S48-D9; S52-Y2; S58-Z4; S67-R6; S73-S8; and S78-G6 (Syngenta Seeds, Henderson, Ky., USA); Richer (Northstar Seed Ltd. Alberta, Calif.); 14RD62 (Stine Seed Co. Ia., USA); or Armor 4744 (Armor Seed, LLC, Ar., USA).

Thus, in a further preferred embodiment, the compounds of Formula (I) (including any one of compounds described in Table 2 (below)), or fungicidal compositions according to the present invention comprising a compound of Formula (I), are used to control *Phakopsora pachyrhizi*, (including fungicidally-resistant strains thereof, as outlined above) on Elite soybean plant varieties where R-gene stacks, conferring a degree of immunity or resistance to specific *Phakopsora pachyrhizi*, have been been introgressed in the plant genome. Numerous benefits may be expected to ensue from said use, e.g. improved biological activity, an advantageous or broader spectrum of activity (inc. sensitive and resistant strains of *Phakopsora pachyrhizi*), an increased safety profile, improved crop tolerance, synergistic interactions or potentiating properties, improved onset of action or a longer lasting residual activity, a reduction in the number of applications and/or a reduction in the application rate of the compounds and compositions required for effective control of the phytopathogen (*Phakopsora pachyrhizi*), thereby enabling beneficial resistance-management practices, reduced environmental impact and reduced operator exposure.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end, they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g., for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be, e.g., fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

The invention provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably, said composition may comprise at least one or more pesticidally active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2, 5-dimethylphenoxymethyl) phenyl]-2-methoxy-iminoacetamide, 4-bromo-2-cyano-N, N-dimethyl-6-trifluoromethylbenzimidazole-1-sulphonamide, a-[N-(3-chloro-2, 6-xylyl)-2-methoxyacetamido]-yl-butyrolactone, 4-chloro-2-cyano-N, -dimethyl-5-p-tolylimidazole-1-sulfonamide, N-allyl-4,5-dimethyl-2-trimethylsilylthiophene-3-carboxamide, N—(I-cyano-1,2-dimethylpropyl)-2-(2,4-dichlorophenoxy) propionamide, N-(2-methoxy-5-pyridyl)-cyclopropane carboxamide, (.+−.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy) pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy) pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy) phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy) phenyl]-3-methoxyacrylate, methyl (E)-2-[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-m ethoxyacrylate, methyl (E)-2-[2-[(3-methyl-pyridin-2-yloxymethyl)phenyl]-3-m ethoxyacrylate, methyl (E)-2-[2-[6-(2-methyl-phenoxy)pyrimidin-4-yloxy]phenyl]-3-m ethoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy) pyrimidin-4-yloxy]phenyl]-3-methoxyacrylate, methyl (E), (E)-2-[2-(5,6-dimethyl pyrazin-2-ylmethyloximinomethyl) phenyl]-3-m ethoxyacrylate, methyl (E)-2-{2-[6-(6-methylpyrid in-2-yloxy)pyrimid in-4-yloxy]phenyl}-3-methoxy-crylate, methyl (E),(E)-2-{2-(3-methoxyphenyl) methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy] phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1, 1'-dioxide, dichlofluanid, diclomezine, dichlone, dicloran, dichlorophen, dichlozoline, diclobutrazol, diclocymet, diethofencarb, difenoconazole, difenzoquat, diflumetorim, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneamino-oxycarbonyl) amino]thio)-ß-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-isopropyl, nuarimol, octhilinone, ofurace, organomercury compounds, orysastrobin, osthol, oxadixyl, oxasulfuron, oxathiapiprolin, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in WO 95/19363 or WO 04/72086, particularly the compounds disclosed therein.

Other examples of such biologically active compounds that the compounds of the invention may be used in combination with include but are not restricted to the following: Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195,RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

The following mixtures of the compounds of Formula (I) with active ingredients are preferred. The abbreviation "TX" means one compound selected from the group consisting of the compounds described in Table 1 (compounds of Formulae (1.a) to (1.ah)) and the compounds described in Table 2 (below):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dino-penton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin 1 (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, Neodiprion sertifer NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, *Bacillus subtilis* var. *amyloliquefaciens* Strain FZB24 (available from Novozymes Biologicals Inc., 5400 Corporate Circle, Salem, Va. 24153, U.S.A. and known under the trade name Taegro®)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis (4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1 (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+

TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium* verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of ametoctradin [865318-97-4]+TX, amisulbrom [348635-87-0]+TX, azaconazole [60207-31-0]+TX, benzovindiflupyr [1072957-71-1]+TX, bitertanol [70585-36-3]+TX, bixafen [581809-46-3]+TX, bromuconazole [116255-48-2]+TX, coumoxystrobin [850881-70-8]+TX, cyproconazole [94361-06-5]+TX, difenoconazole [119446-68-3]+TX, diniconazole [83657-24-3]+TX, enoxastrobin [238410-11-2]+TX, epoxiconazole [106325-08-0]+TX, fenbuconazole [114369-43-6]+TX, fenpyrazamine [473798-59-3]+TX, fluquinconazole [136426-54-5]+TX, flusilazole [85509-19-9]+TX, flutriafol [76674-21-0]+TX, fluxapyroxad [907204-31-3]+TX, fluopyram [658066-35-4]+TX, fenaminstrobin [366815-39-6]+TX, isofetamid [875915-78-9]+TX, hexaconazole [79983-71-4]+TX, imazalil [35554-44-0]+TX, imibenconazole [86598-92-7]+TX, ipconazole [125225-28-7]+TX, ipfentrifluconazole [1417782-08-1]+TX, isotianil [224049-04-1]+TX, mandestrobin [173662-97-0] (can be prepared according to the procedures described in WO 2010/093059)+TX, mefentrifluconazole [1417782-03-6]+TX, metconazole [125116-23-6]+TX, myclobutanil [88671-89-0]+TX, paclobutrazol [76738-62-0]+TX, pefurazoate [101903-30-4]+TX, penflufen [494793-67-8]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidin [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, fluindapyr [1383809-87-7]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, flutianil [958647-10-4]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, pyraoxystrobin [862588-11-2]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, picarbutrazox [500207-04-5]+TX, polyoxins [11113-80-7]+TX, probenazole [27605-76-1]+TX, propamocarb [25606-41-1]+TX, proquinazid [189278-12-4]+TX, pydiflumetofen [1228284-64-7]+TX, pyrametostrobin [915410-70-7]+TX, pyroquilon [57369-32-1]+TX, pyriofenone [688046-61-9]+TX, pyribencarb [799247-52-2]+TX, pyrisoxazole [847749-37-5]+TX, quinoxyfen [124495-18-7]+TX, quintozene [82-68-8]+TX, sulfur [7704-34-9]+TX, Timorex Gold™ (plant extract containing tea tree oil from the Stockton Group)+TX, tebufloquin [376645-78-2]+TX, tiadinil [223580-51-6]+TX, triazoxide [72459-58-6]+TX, tolprocarb [911499-62-2]+TX, triclopyricarb [902760-40-1]+TX, tricyclazole [41814-78-2]+TX, triforine [26644-46-2]+TX, validamycin [37248-47-8]+TX, valifenalate [283159-90-0]+TX, zoxamide (RH7281) [156052-68-5]+TX, mandipropamid [374726-62-2]+TX, isopyrazam [881685-58-1]+

TX, phenamacril+TX, sedaxane [874967-67-6]+TX, trinexapac-ethyl [95266-40-3]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H, 11 Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX, or a biologically active compound selected from the group consisting of N-[(5-chloro-2-isopropyl-phenyl)methyl]-N-cyclopropyl-3-(difluoromethyl)-5-fluoro-1-methyl-pyrazole-4-carboxamide (can be prepared according to the procedures described in WO 2010/130767)+TX, 2,6-Dimethyl-1H,5H-[1,4]dithiino[2,3-c:5,6-c']dipyrrole-1,3,5,7(2H,6H)-tetrone (can be prepared according to the procedures described in WO 2011/138281)+TX, 6-ethyl-5,7-dioxo-pyrrolo[4,5][1,4]dithiino[1,2-c]isothiazole-3-carbonitrile+TX, 4-(2-bromo-4-fluoro-phenyl)-N-(2-chloro-6-fluoro-phenyl)-2,5-dimethyl-pyrazazol-3-amine (can be prepared according to the procedures described in WO 2012/031061)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, CAS 850881-30-0+TX, 3-(3,4-dichloro-1,2-thiazol-5-ylmethoxy)-1,2-benzothiazole 1,1-dioxide (can be prepared according to the procedures described in WO 2007/129454)+TX, 2-[2-[(2,5-dimethylphenoxy)methyl]phenyl]-2-methoxy-N-methyl-acetamide+TX, 3-(4,4-difluoro-3,4-dihydro-3,3-dimethylisoquinolin-1-yl)quinolone (can be prepared according to the procedures described in WO 2005/070917)+TX, 2-[2-fluoro-6-[(8-fluoro-2-methyl-3-quinolyl)oxy]phenyl]propan-2-ol (can be prepared according to the procedures described in WO 2011/081174)+TX, 2-[2-[(7,8-difluoro-2-methyl-3-quinolyl)oxy]-6-fluoro-phenyl]propan-2-ol (can be prepared according to the procedures described in WO 2011/081174)+TX, oxathiapiprolin+TX [1003318-67-9], tert-butyl N-[6-[[[(1-methyltetrazol-5-yl)-phenyl-methylene]amino]oxymethyl]-2-pyridyl]carbamate+TX, N-[2-(3,4-difluorophenyl)phenyl]-3-(trifluoromethyl)pyrazine-2-carboxamide (can be prepared according to the procedures described in WO 2007/072999)+TX, 3-(difluoromethyl)-1-methyl-N-[(3R)-1,1,3-trimethylindan-4-yl]pyrazole-4-carboxamide (can be prepared according to the procedures described in WO 2014/013842)+TX, 2,2,2-trifluoroethyl N-[2-methyl-1-[[(4-methylbenzoyl)amino]methyl]propyl]carbamate+TX, (2RS)-2-[4-(4-chlorophenoxy)-α,α,α-trifluoro-o-tolyl]-1-(1H-1,2,4-triazol-1-yl)propan-2-ol+TX, (2RS)-2-[4-(4-chlorophenoxy)-α,α,α-trifluoro-o-tolyl]-3-methyl-1-(1H-1,2,4-triazol-1-yl)butan-2-ol+TX, 2-(difluoromethyl)-N-[(3R)-3-ethyl-1,1-dimethyl-indan-4-yl]pyridine-3-carboxamide+TX, 2-(difluoromethyl)-N-[3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine (can be prepared according to the procedures described in WO 2007/031513)+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate (can be prepared according to the procedures described in WO 2012/025557)+TX, but-3-ynyl N-[6-[[(Z)-[(1-methyltetrazol-5-yl)-phenyl-methylene]amino]oxymethyl]-2-pyridyl]carbamate (can be prepared according to the procedures described in WO 2010/000841)+TX, 2-[[3-(2-chlorophenyl)-2-(2,4-difluorophenyl)oxiran-2-yl]methyl]-4H-1,2,4-triazole-3-thione (can be prepared according to the procedures described in WO 2010/146031)+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine (can be prepared according to the procedures described in WO 2005/121104)+TX, 2-[2-chloro-4-(4-chlorophenoxy) phenyl]-1-(1,2,4-triazol-1-yl)propan-2-ol (can be prepared according to the procedures described in WO 2013/024082)+TX, 3-chloro-4-(2,6-difluorophenyl)-6-methyl-5-phenyl-pyridazine (can be prepared according to the procedures described in WO 2012/020774)+TX, 4-(2,6-difluorophenyl)-6-methyl-5-phenyl-pyridazine-3-carbonitrile (can be prepared according to the procedures described in WO 2012/020774)+TX, (R)-3-(difluoromethyl)-1-methyl-N-[1,1,3-trimethylindan-4-yl]pyrazole-4-carboxamide (can be prepared according to the procedures described in WO 2011/162397)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, 1-[2-[[1-(4-chlorophenyl)pyrazol-3-yl]oxymethyl]-3-methyl-phenyl]-4-methyl-tetrazol-5-one (can be prepared according to the procedures described in WO 2013/162072)+TX, 1-methyl-4-[3-methyl-2-[[2-methyl-4-(3,4,5-trimethylpyrazol-1-yl)phenoxy]methyl]phenyl]tetrazol-5-one (can be prepared according to the procedures described in WO 2014/051165)+TX, (Z,2E)-5-[1-(4-chlorophenyl)pyrazol-3-yl]oxy-2-methoxyimino-N,3-dimethyl-pent-3-enamide+TX, (4-phenoxyphenyl)methyl 2-amino-6-methyl-pyridine-3-carboxylate+TX, N-(5-chloro-2-isopropylbenzyl)-N-cyclopropyl-3-(difluoromethyl)-5-fluoro-1-methylpyrazole-4-carboxamide [1255734-28-1] (can be prepared according to the procedures described in WO 2010/130767)+TX, 3-(difluoromethyl)-N—[(R)-2,3-dihydro-1,1,3-trimethyl-1H-inden-4-yl]-1-methylpyrazole-4-carboxamide [1352994-67-2]+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX,

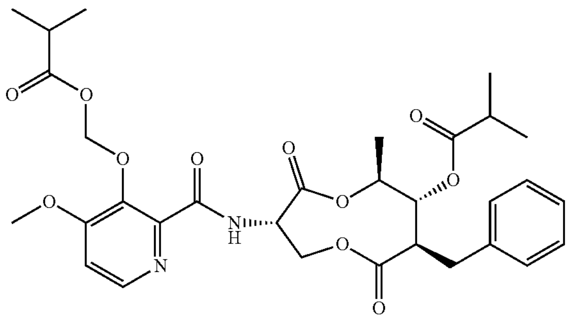 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

(fenpicoxamid [517875-34-2])+TX (as described in WO 2003/035617), 2-(difluoromethyl)-N-(1,1,3-trimethylindan-4-yl)pyridine-3-carboxamide+TX, 2-(difluoromethyl)-N-(3-ethyl-1,1-dimethyl-indan-4-yl)pyridine-3-carboxamide+TX, 2-(difluoromethyl)-N-(1,1-dimethyl-3-propyl-indan-4-yl)pyridine-3-carboxamide+TX, 2-(difluoromethyl)-N-(3-isobutyl-1,1-dimethyl-indan-4-yl)pyridine-3-carboxamide+TX, 2-(difluoromethyl)-N-[(3R)-1,1,3-trimethylindan-4-yl] pyridine-3-carboxamide+TX, 2-(difluoromethyl)-N-[(3R)-3-ethyl-1,1-dimethyl-indan-4-yl]pyridine-3-carboxamide+TX, and 2-(difluoromethyl)-N-[(3R)-1,1-dimethyl-3-propyl-indan-4-yl]pyridine-3-carboxamide+TX, wherein each of these carboxamide compounds can be prepared according to the procedures described in WO 2014/095675 and/or WO 2016/139189.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of a compound of Formula (I) as described in Table 1 (a compound of Formulae (1.a) to (1.ah)) or a compound of Formula (I) described in Table 2 (below) and another active ingredient as described above are preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of Formula (I) as described in Table 1 (a compound of Formulae (1.a) to (1.ah)) or a compound of Formula (I) described in Table 2 (below), and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compound of Formula (I) as described in Table 1 (a compound of Formulae (1.a) to (1.ah)) or a compound of Formula (I) described in Table 2 (below) and the active ingredient(s) as described above, is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds of Formula (I) for the preparation of these compositions are also a subject of the invention.

Another aspect of invention is related to the use of a compound of formula (I) or of a preferred individual compound as above-defined, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g., harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g. harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g., in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g., by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g., as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

TABLE 1

Examples of individual compounds of formula (I) according to the invention.

| Compound No. | $R^1$ | $R^2$ | $R^4$ | $R^5$ | $R^6$ | $R^7$ |
|---|---|---|---|---|---|---|
| 001 | $CH_3$ | OH | $CH_3$ | $CH_3$ | $CH_3$ | $CH_3$ |
| 002 | $CH_3$ | OH | $CH_3$ | $CH_3$ | $CH_3$ | $CH_2CH_3$ |
| 003 | $CH_3$ | OH | $CH_3$ | $CH_3$ | $CH_2CH_3$ | $CH_2CH_3$ |
| 004 | $CH_3$ | OH | $CH_3$ | $CH_3$ | $CH_3$ | $CH(CH_3)_2$ |
| 005 | $CH_3$ | OH | $CH_3$ | $CH_3$ | $CH_3$ | cyclopropyl |
| 006 | $CH_3$ | OH | $CH_3$ | $CH_3$ | —$CH_2CH_2$— | |
| 007 | $CH_3$ | OH | $CH_3$ | $CH_3$ | —$CF_2CH_2$— | |
| 008 | $CH_3$ | OH | $CH_3$ | $CH_3$ | —$CH(CH(CH_3)_2)CH_2$— | |
| 009 | $CH_3$ | OH | $CH_3$ | $CH_3$ | —CH(cyclopropyl)$CH_2$— | |
| 010 | $CH_3$ | OH | $CH_3$ | $CH_3$ | —CH(Ph)$CH_2$— | |
| 011 | $CH_3$ | OH | $CH_3$ | $CH_3$ | —CH(4-F—Ph)$CH_2$— | |
| 012 | $CH_3$ | OH | $CH_3$ | $CH_3$ | —$CH_2CH_2CH_2$— | |
| 013 | $CH_3$ | OH | $CH_3$ | $CH_3$ | —$CH_2$CH(Ph)$CH_2$— | |
| 014 | $CH_3$ | OH | $CH_3$ | $CH_3$ | —$CH_2CH_2CH_2CH_2$— | |
| 015 | $CH_3$ | OH | $CH_3$ | $CH_3$ | —$CH_2CH_2CH_2CH_2CH_2$— | |
| 016 | $CH_3$ | OH | $CH_3$ | $CH_2CH_3$ | $CH_3$ | $CH_3$ |
| 017 | $CH_3$ | OH | $CH_3$ | $CH_2CH_3$ | $CH_3$ | $CH_2CH_3$ |
| 018 | $CH_3$ | OH | $CH_3$ | $CH_2CH_3$ | $CH_2CH_3$ | $CH_2CH_3$ |
| 019 | $CH_3$ | OH | $CH_3$ | $CH_2CH_3$ | $CH_3$ | $CH(CH_3)_2$ |
| 020 | $CH_3$ | OH | $CH_3$ | $CH_2CH_3$ | $CH_3$ | cyclopropyl |
| 021 | $CH_3$ | OH | $CH_3$ | $CH_2CH_3$ | —$CH_2CH_2$— | |
| 022 | $CH_3$ | OH | $CH_3$ | $CH_2CH_3$ | —$CF_2CH_2$— | |
| 023 | $CH_3$ | OH | $CH_3$ | $CH_2CH_3$ | —$CH(CH(CH_3)_2)CH_2$— | |
| 024 | $CH_3$ | OH | $CH_3$ | $CH_2CH_3$ | —CH(cyclopropyl)$CH_2$— | |
| 025 | $CH_3$ | OH | $CH_3$ | $CH_2CH_3$ | —CH(Ph)$CH_2$— | |
| 026 | $CH_3$ | OH | $CH_3$ | $CH_2CH_3$ | —CH(4-F—Ph)$CH_2$— | |
| 027 | $CH_3$ | OH | $CH_3$ | $CH_2CH_3$ | —$CH_2CH_2CH_2$— | |
| 028 | $CH_3$ | OH | $CH_3$ | $CH_2CH_3$ | —$CH_2$CH(Ph)$CH_2$— | |
| 029 | $CH_3$ | OH | $CH_3$ | $CH_2CH_3$ | —$CH_2CH_2CH_2CH_2$— | |
| 030 | $CH_3$ | OH | $CH_3$ | $CH_2CH_3$ | —$CH_2CH_2CH_2CH_2CH_2$— | |
| 031 | $CH_3$ | OH | $CH_2CH_3$ | $CH_3$ | $CH_3$ | $CH_3$ |
| 032 | $CH_3$ | OH | $CH_2CH_3$ | $CH_3$ | $CH_3$ | $CH_2CH_3$ |
| 033 | $CH_3$ | OH | $CH_2CH_3$ | $CH_3$ | $CH_2CH_3$ | $CH_2CH_3$ |
| 034 | $CH_3$ | OH | $CH_2CH_3$ | $CH_3$ | $CH_3$ | $CH(CH_3)_2$ |
| 035 | $CH_3$ | OH | $CH_2CH_3$ | $CH_3$ | $CH_3$ | cyclopropyl |
| 036 | $CH_3$ | OH | $CH_2CH_3$ | $CH_3$ | —$CH_2CH_2$— | |
| 037 | $CH_3$ | OH | $CH_2CH_3$ | $CH_3$ | —$CF_2CH_2$— | |
| 038 | $CH_3$ | OH | $CH_2CH_3$ | $CH_3$ | —$CH(CH(CH_3)_2)CH_2$— | |
| 039 | $CH_3$ | OH | $CH_2CH_3$ | $CH_3$ | —CH(cyclopropyl)$CH_2$— | |
| 040 | $CH_3$ | OH | $CH_2CH_3$ | $CH_3$ | —CH(Ph)$CH_2$— | |
| 041 | $CH_3$ | OH | $CH_2CH_3$ | $CH_3$ | —CH(4-F—Ph)$CH_2$— | |
| 042 | $CH_3$ | OH | $CH_2CH_3$ | $CH_3$ | —$CH_2CH_2CH_2$— | |
| 043 | $CH_3$ | OH | $CH_2CH_3$ | $CH_3$ | —$CH_2$CH(Ph)$CH_2$— | |
| 044 | $CH_3$ | OH | $CH_2CH_3$ | $CH_3$ | —$CH_2CH_2CH_2CH_2$— | |
| 045 | $CH_3$ | OH | $CH_2CH_3$ | $CH_3$ | —$CH_2CH_2CH_2CH_2CH_2$— | |
| 046 | $CH_3$ | OH | $CH_3$ | $CH_3$ | $CH_3$ | $CH_3$ |
| 047 | $CH_3$ | OH | $CH_3$ | $CH_3$ | $CH_3$ | $CH_2CH_3$ |
| 048 | $CH_3$ | OH | $CH_3$ | $CH_3$ | $CH_2CH_3$ | $CH_2CH_3$ |
| 049 | $CH_3$ | OH | $CH_3$ | $CH_3$ | $CH_3$ | $CH(CH_3)_2$ |
| 050 | $CH_3$ | OH | $CH_3$ | $CH_3$ | $CH_3$ | cyclopropyl |
| 051 | $CH_3$ | OH | $CH_3$ | $CH_3$ | —$CH_2CH_2$— | |
| 052 | $CH_3$ | OH | $CH_3$ | $CH_3$ | —$CF_2CH_2$— | |
| 053 | $CH_3$ | OH | $CH_3$ | $CH_3$ | —$CH(CH(CH_3)_2)CH_2$— | |
| 054 | $CH_3$ | OH | $CH_3$ | $CH_3$ | —CH(cyclopropyl)$CH_2$— | |
| 055 | $CH_3$ | OH | $CH_3$ | $CH_3$ | —CH(Ph)$CH_2$— | |
| 056 | $CH_3$ | OH | $CH_3$ | $CH_3$ | —CH(4-F—Ph)$CH_2$— | |
| 057 | $CH_3$ | OH | $CH_3$ | $CH_3$ | —$CH_2CH_2CH_2$— | |
| 058 | $CH_3$ | OH | $CH_3$ | $CH_3$ | —$CH_2$CH(Ph)$CH_2$— | |
| 059 | $CH_3$ | OH | $CH_3$ | $CH_3$ | —$CH_2CH_2CH_2CH_2$— | |

TABLE 1-continued

Examples of individual compounds of formula (I) according to the invention.

| Compound No. | $R^1$ | $R^2$ | $R^4$ | $R^5$ | $R^6$ | $R^7$ |
|---|---|---|---|---|---|---|
| 060 | $CH_3$ | OH | $CH_3$ | $CH_3$ | $-CH_2CH_2CH_2CH_2CH_2-$ | |
| 061 | $CH_3$ | $OC(=O)CH_3$ | $CH_3$ | $CH_3$ | $CH_3$ | $CH_3$ |
| 062 | $CH_3$ | $OC(=O)CH_3$ | $CH_3$ | $CH_3$ | $CH_3$ | $CH_2CH_3$ |
| 063 | $CH_3$ | $OC(=O)CH_3$ | $CH_3$ | $CH_3$ | $CH_2CH_3$ | $CH_2CH_3$ |
| 064 | $CH_3$ | $OC(=O)CH_3$ | $CH_3$ | $CH_3$ | $CH_3$ | $CH(CH_3)_2$ |
| 065 | $CH_3$ | $OC(=O)CH_3$ | $CH_3$ | $CH_3$ | $CH_3$ | cyclopropyl |
| 066 | $CH_3$ | $OC(=O)CH_3$ | $CH_3$ | $CH_3$ | $-CH_2CH_2-$ | |
| 067 | $CH_3$ | $OC(=O)CH_3$ | $CH_3$ | $CH_3$ | $-CF_2CH_2-$ | |
| 068 | $CH_3$ | $OC(=O)CH_3$ | $CH_3$ | $CH_3$ | $-CH(CH(CH_3)_2)CH_2-$ | |
| 069 | $CH_3$ | $OC(=O)CH_3$ | $CH_3$ | $CH_3$ | $-CH(\text{cyclopropyl})CH_2-$ | |
| 070 | $CH_3$ | $OC(=O)CH_3$ | $CH_3$ | $CH_3$ | $-CH(Ph)CH_2-$ | |
| 071 | $CH_3$ | $OC(=O)CH_3$ | $CH_3$ | $CH_3$ | $-CH(4-F-Ph)CH_2-$ | |
| 072 | $CH_3$ | $OC(=O)CH_3$ | $CH_3$ | $CH_3$ | $-CH_2CH_2CH_2-$ | |
| 073 | $CH_3$ | $OC(=O)CH_3$ | $CH_3$ | $CH_3$ | $-CH_2CH(Ph)CH_2-$ | |
| 074 | $CH_3$ | $OC(=O)CH_3$ | $CH_3$ | $CH_3$ | $-CH_2CH_2CH_2CH_2-$ | |
| 075 | $CH_3$ | $OC(=O)CH_3$ | $CH_3$ | $CH_3$ | $-CH_2CH_2CH_2CH_2CH_2-$ | |
| 076 | $CH_3$ | $OC(=O)CH_2CH_3$ | $CH_3$ | $CH_3$ | $CH_3$ | $CH_3$ |
| 077 | $CH_3$ | $OC(=O)CH_2CH_3$ | $CH_3$ | $CH_3$ | $CH_3$ | $CH_2CH_3$ |
| 078 | $CH_3$ | $OC(=O)CH_2CH_3$ | $CH_3$ | $CH_3$ | $CH_2CH_3$ | $CH_2CH_3$ |
| 079 | $CH_3$ | $OC(=O)CH_2CH_3$ | $CH_3$ | $CH_3$ | $CH_3$ | $CH(CH_3)_2$ |
| 080 | $CH_3$ | $OC(=O)CH_2CH_3$ | $CH_3$ | $CH_3$ | $CH_3$ | cyclopropyl |
| 081 | $CH_3$ | $OC(=O)CH_2CH_3$ | $CH_3$ | $CH_3$ | $-CH_2CH_2-$ | |
| 082 | $CH_3$ | $OC(=O)CH_2CH_3$ | $CH_3$ | $CH_3$ | $-CF_2CH_2-$ | |
| 083 | $CH_3$ | $OC(=O)CH_2CH_3$ | $CH_3$ | $CH_3$ | $-CH(CH(CH_3)_2)CH_2-$ | |
| 084 | $CH_3$ | $OC(=O)CH_2CH_3$ | $CH_3$ | $CH_3$ | $-CH(\text{cyclopropyl})CH_2-$ | |
| 085 | $CH_3$ | $OC(=O)CH_2CH_3$ | $CH_3$ | $CH_3$ | $-CH(Ph)CH_2-$ | |
| 086 | $CH_3$ | $OC(=O)CH_2CH_3$ | $CH_3$ | $CH_3$ | $-CH(4-F-Ph)CH_2-$ | |
| 087 | $CH_3$ | $OC(=O)CH_2CH_3$ | $CH_3$ | $CH_3$ | $-CH_2CH_2CH_2-$ | |
| 088 | $CH_3$ | $OC(=O)CH_2CH_3$ | $CH_3$ | $CH_3$ | $-CH_2CH(Ph)CH_2-$ | |
| 089 | $CH_3$ | $OC(=O)CH_2CH_3$ | $CH_3$ | $CH_3$ | $-CH_2CH_2CH_2CH_2-$ | |
| 090 | $CH_3$ | $OC(=O)CH_2CH_3$ | $CH_3$ | $CH_3$ | $-CH_2CH_2CH_2CH_2CH_2-$ | |
| 091 | $CH_3$ | $OCH_2OC(=O)CH_3$ | $CH_3$ | $CH_3$ | $CH_3$ | $CH_3$ |
| 092 | $CH_3$ | $OCH_2OC(=O)CH_3$ | $CH_3$ | $CH_3$ | $CH_3$ | $CH_2CH_3$ |
| 093 | $CH_3$ | $OCH_2OC(=O)CH_3$ | $CH_3$ | $CH_3$ | $CH_2CH_3$ | $CH_2CH_3$ |
| 094 | $CH_3$ | $OCH_2OC(=O)CH_3$ | $CH_3$ | $CH_3$ | $CH_3$ | $CH(CH_3)_2$ |
| 095 | $CH_3$ | $OCH_2OC(=O)CH_3$ | $CH_3$ | $CH_3$ | $CH_3$ | cyclopropyl |
| 096 | $CH_3$ | $OCH_2OC(=O)CH_3$ | $CH_3$ | $CH_3$ | $-CH_2CH_2-$ | |
| 097 | $CH_3$ | $OCH_2OC(=O)CH_3$ | $CH_3$ | $CH_3$ | $-CF_2CH_2-$ | |
| 098 | $CH_3$ | $OCH_2OC(=O)CH_3$ | $CH_3$ | $CH_3$ | $-CH(CH(CH_3)_2)CH_2-$ | |
| 099 | $CH_3$ | $OCH_2OC(=O)CH_3$ | $CH_3$ | $CH_3$ | $-CH(\text{cyclopropyl})CH_2-$ | |
| 100 | $CH_3$ | $OCH_2OC(=O)CH_3$ | $CH_3$ | $CH_3$ | $-CH(Ph)CH_2-$ | |
| 101 | $CH_3$ | $OCH_2OC(=O)CH_3$ | $CH_3$ | $CH_3$ | $-CH(4-F-Ph)CH_2-$ | |
| 102 | $CH_3$ | $OCH_2OC(=O)CH_3$ | $CH_3$ | $CH_3$ | $-CH_2CH_2CH_2-$ | |
| 103 | $CH_3$ | $OCH_2OC(=O)CH_3$ | $CH_3$ | $CH_3$ | $-CH_2CH(Ph)CH_2-$ | |
| 104 | $CH_3$ | $OCH_2OC(=O)CH_3$ | $CH_3$ | $CH_3$ | $-CH_2CH_2CH_2CH_2-$ | |
| 105 | $CH_3$ | $OCH_2OC(=O)CH_3$ | $CH_3$ | $CH_3$ | $-CH_2CH_2CH_2CH_2CH_2-$ | |
| 106 | $CH_3$ | $OCH_2OC(=O)CH(CH_3)_2$ | $CH_3$ | $CH_3$ | $CH_3$ | $CH_3$ |
| 107 | $CH_3$ | $OCH_2OC(=O)CH(CH_3)_2$ | $CH_3$ | $CH_3$ | $CH_3$ | $CH_2CH_3$ |
| 108 | $CH_3$ | $OCH_2OC(=O)CH(CH_3)_2$ | $CH_3$ | $CH_3$ | $CH_2CH_3$ | $CH_2CH_3$ |
| 109 | $CH_3$ | $OCH_2OC(=O)CH(CH_3)_2$ | $CH_3$ | $CH_3$ | $CH_3$ | $CH(CH_3)_2$ |
| 110 | $CH_3$ | $OCH_2OC(=O)CH(CH_3)_2$ | $CH_3$ | $CH_3$ | $CH_3$ | cyclopropyl |
| 111 | $CH_3$ | $OCH_2OC(=O)CH(CH_3)_2$ | $CH_3$ | $CH_3$ | $-CH_2CH_2-$ | |
| 112 | $CH_3$ | $OCH_2OC(=O)CH(CH_3)_2$ | $CH_3$ | $CH_3$ | $-CF_2CH_2-$ | |
| 113 | $CH_3$ | $OCH_2OC(=O)CH(CH_3)_2$ | $CH_3$ | $CH_3$ | $-CH(CH(CH_3)_2)CH_2-$ | |
| 114 | $CH_3$ | $OCH_2OC(=O)CH(CH_3)_2$ | $CH_3$ | $CH_3$ | $-CH(\text{cyclopropyl})CH_2-$ | |
| 115 | $CH_3$ | $OCH_2OC(=O)CH(CH_3)_2$ | $CH_3$ | $CH_3$ | $-CH(Ph)CH_2-$ | |
| 116 | $CH_3$ | $OCH_2OC(=O)CH(CH_3)_2$ | $CH_3$ | $CH_3$ | $-CH(4-F-Ph)CH_2-$ | |
| 117 | $CH_3$ | $OCH_2OC(=O)CH(CH_3)_2$ | $CH_3$ | $CH_3$ | $-CH_2CH_2CH_2-$ | |
| 118 | $CH_3$ | $OCH_2OC(=O)CH_2CH_3$ | $CH_3$ | $CH_3$ | $-CH_2CH(Ph)CH_2-$ | |
| 119 | $CH_3$ | $OCH_2OC(=O)CH_2CH_3$ | $CH_3$ | $CH_3$ | $-CH_2CH_2CH_2CH_2-$ | |
| 120 | $CH_3$ | $OCH_2OC(=O)CH_2CH_3$ | $CH_3$ | $CH_3$ | $-CH_2CH_2CH_2CH_2CH_2-$ | |
| 121 | $CH_3$ | $OCH_2OC(=O)CH(CH_3)_2$ | $CH_3$ | $CH_3$ | $CH_3$ | $CH_3$ |
| 122 | $CH_3$ | $OCH_2OC(=O)CH(CH_3)_2$ | $CH_3$ | $CH_3$ | $CH_3$ | $CH_2CH_3$ |
| 123 | $CH_3$ | $OCH_2OC(=O)CH(CH_3)_2$ | $CH_3$ | $CH_3$ | $CH_2CH_3$ | $CH_2CH_3$ |
| 124 | $CH_3$ | $OCH_2OC(=O)CH(CH_3)_2$ | $CH_3$ | $CH_3$ | $CH_3$ | $CH(CH_3)_2$ |
| 125 | $CH_3$ | $OCH_2OC(=O)CH(CH_3)_2$ | $CH_3$ | $CH_3$ | $CH_3$ | cyclopropyl |
| 126 | $CH_3$ | $OCH_2OC(=O)CH(CH_3)_2$ | $CH_3$ | $CH_3$ | $-CH_2CH_2-$ | |
| 127 | $CH_3$ | $OCH_2OC(=O)CH(CH_3)_2$ | $CH_3$ | $CH_3$ | $-CF_2CH_2-$ | |
| 128 | $CH_3$ | $OCH_2OC(=O)CH(CH_3)_2$ | $CH_3$ | $CH_3$ | $-CH(CH(CH_3)_2)CH_2-$ | |
| 129 | $CH_3$ | $OCH_2OC(=O)CH(CH_3)_2$ | $CH_3$ | $CH_3$ | $-CH(\text{cyclopropyl})CH_2-$ | |
| 130 | $CH_3$ | $OCH_2OC(=O)CH(CH_3)_2$ | $CH_3$ | $CH_3$ | $-CH(Ph)CH_2-$ | |
| 131 | $CH_3$ | $OCH_2OC(=O)CH(CH_3)_2$ | $CH_3$ | $CH_3$ | $-CH(4-F-Ph)CH_2-$ | |
| 132 | $CH_3$ | $OCH_2OC(=O)CH(CH_3)_2$ | $CH_3$ | $CH_3$ | $-CH_2CH_2CH_2-$ | |
| 133 | $CH_3$ | $OCH_2OC(=O)CH(CH_3)_2$ | $CH_3$ | $CH_3$ | $-CH_2CH(Ph)CH_2-$ | |
| 134 | $CH_3$ | $OCH_2OC(=O)CH(CH_3)_2$ | $CH_3$ | $CH_3$ | $-CH_2CH_2CH_2CH_2-$ | |

TABLE 1-continued

Examples of individual compounds of formula (I) according to the invention.

| Compound No. | $R^1$ | $R^2$ | $R^4$ | $R^5$ | $R^6$ | $R^7$ |
|---|---|---|---|---|---|---|
| 135 | $CH_3$ | $OCH_2OC({=}O)CH(CH_3)_2$ | $CH_3$ | $CH_3$ | $—CH_2CH_2CH_2CH_2CH_2—$ | |
| 136 | $CH_2CH_3$ | OH | $CH_3$ | $CH_3$ | $CH_3$ | $CH_3$ |
| 137 | $CH_2CH_3$ | OH | $CH_3$ | $CH_3$ | $CH_3$ | $CH_2CH_3$ |
| 138 | $CH_2CH_3$ | OH | $CH_3$ | $CH_3$ | $CH_2CH_3$ | $CH_2CH_3$ |
| 139 | $CH_2CH_3$ | OH | $CH_3$ | $CH_3$ | $CH_3$ | $CH(CH_3)_2$ |
| 140 | $CH_2CH_3$ | OH | $CH_3$ | $CH_3$ | $CH_3$ | cyclopropyl |
| 141 | $CH_2CH_3$ | OH | $CH_3$ | $CH_3$ | $—CH_2CH_2—$ | |
| 142 | $CH_2CH_3$ | OH | $CH_3$ | $CH_3$ | $—CF_2CH_2—$ | |
| 143 | $CH_2CH_3$ | OH | $CH_3$ | $CH_3$ | $—CH(CH(CH_3)_2)CH_2—$ | |
| 144 | $CH_2CH_3$ | OH | $CH_3$ | $CH_3$ | $—CH(cyclopropyl)CH_2—$ | |
| 145 | $CH_2CH_3$ | OH | $CH_3$ | $CH_3$ | $—CH(Ph)CH_2—$ | |
| 146 | $CH_2CH_3$ | OH | $CH_3$ | $CH_3$ | $—CH(4\text{-}F—Ph)CH_2—$ | |
| 147 | $CH_2CH_3$ | OH | $CH_3$ | $CH_3$ | $—CH_2CH_2CH_2—$ | |
| 148 | $CH_2CH_3$ | OH | $CH_3$ | $CH_3$ | $—CH_2CH(Ph)CH_2—$ | |
| 149 | $CH_2CH_3$ | OH | $CH_3$ | $CH_3$ | $—CH_2CH_2CH_2CH_2—$ | |
| 150 | $CH_2CH_3$ | OH | $CH_3$ | $CH_3$ | $—CH_2CH_2CH_2CH_2CH_2—$ | |

Wherein there are:

a) 150 compounds of formula (I.a):

(I.a)

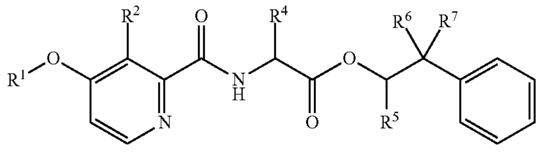

wherein $R^1$, $R^2$, $R^4$, $R^5$, $R^6$ and $R^7$ are as defined in Table 1.

b) 150 compounds of formula (I.b):

(I.b)

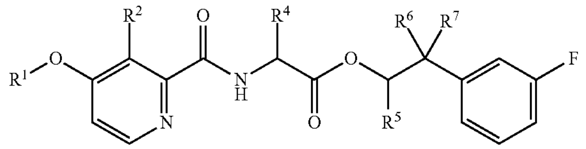

wherein $R^1$, $R^2$, $R^4$, $R^5$, $R^6$ and $R^7$ are as defined in Table 1.

c) 150 compounds of formula (I.c):

(I.c)

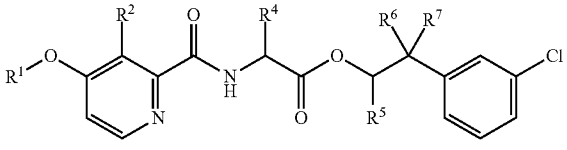

wherein $R^1$, $R^2$, $R^4$, $R^5$, $R^6$ and $R^7$ are as defined in Table 1.

d) 150 compounds of formula (I.d):

(I.d)

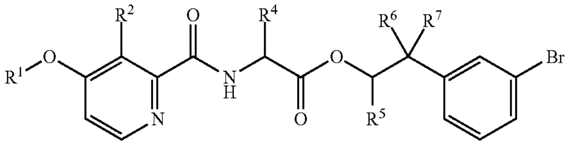

wherein $R^1$, $R^2$, $R^4$, $R^5$, $R^6$ and $R^7$ are as defined in Table 1.

e) 150 compounds of formula (I.e):

(I.e)

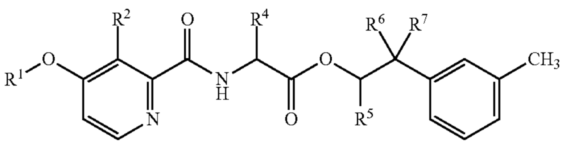

wherein $R^1$, $R^2$, $R^4$, $R^5$, $R^6$ and $R^7$ are as defined in Table 1.

f) 150 compounds of formula (I.f):

(I.f)

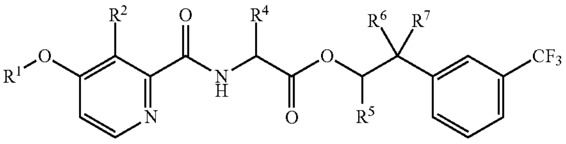

wherein $R^1$, $R^2$, $R^4$, $R^5$, $R^6$ and $R^7$ are as defined in Table 1.

g) 150 compounds of formula (I.g):

(I.g)

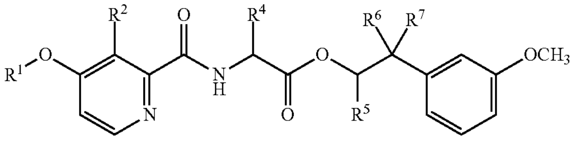

wherein $R^1$, $R^2$, $R^4$, $R^5$, $R^6$ and $R^7$ are as defined in Table 1.

h) 150 compounds of formula (I.h):

(I.h)

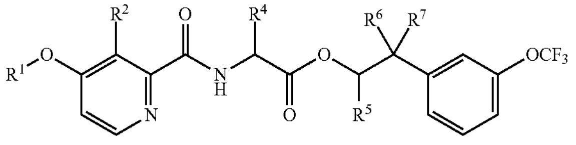

Wherein $R^1$, $R^2$, $R^4$, $R^5$, $R^6$ and $R^7$ are as defined in Table 1.

i) 150 compounds of formula (I.i):

(I.i)

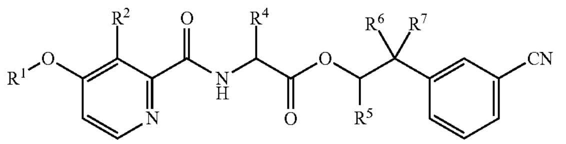

wherein $R^1$, $R^2$, $R^4$, $R^5$, $R^6$ and $R^7$ are as defined in Table 1.

j) 150 compounds of formula (I.j):

(I.j)

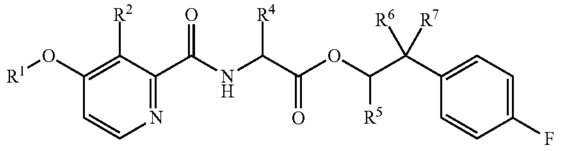

wherein $R^1$, $R^2$, $R^4$, $R^5$, $R^6$ and $R^7$ are as defined in Table 1.

k) 150 compounds of formula (I.k):

(I.k)

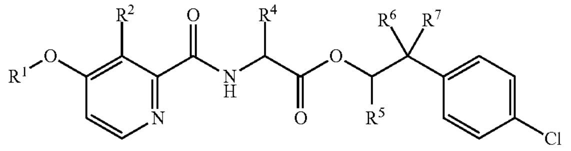

wherein $R^1$, $R^2$, $R^4$, $R^5$, $R^6$ and $R^7$ are as defined in Table 1.

m) 150 compounds of formula (I.m):

(I.m)

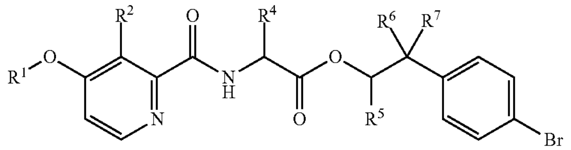

wherein $R^1$, $R^2$, $R^4$, $R^5$, $R^6$ and $R^7$ are as defined in Table 1.

n) 150 compounds of formula (I.n):

(I.n)

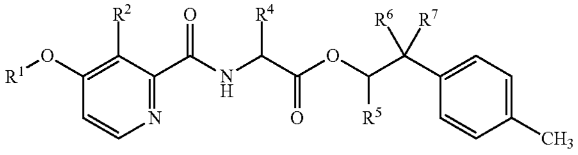

wherein $R^1$, $R^2$, $R^4$, $R^5$, $R^6$ and $R^7$ are as defined in Table 1.

o) 150 compounds of formula (I.o):

(I.o)

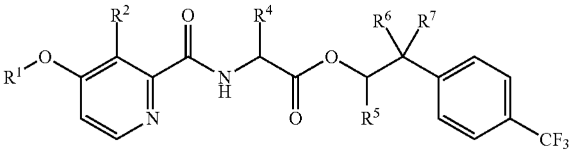

wherein $R^1$, $R^2$, $R^4$, $R^5$, $R^6$ and $R^7$ are as defined in Table 1.

p) 150 compounds of formula (I.p):

(I.p)

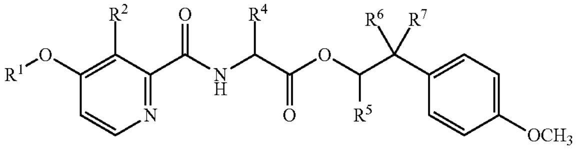

wherein $R^1$, $R^2$, $R^4$, $R^5$, $R^6$ and $R^7$ are as defined in Table 1.

q) 150 compounds of formula (I.q):

(I.q)

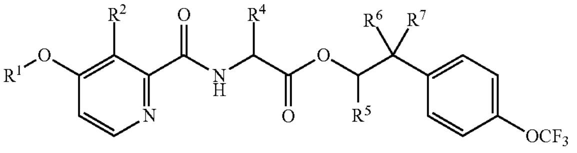

wherein $R^1$, $R^2$, $R^4$, $R^5$, $R^6$ and $R^7$ are as defined in Table 1.

r) 150 compounds of formula (I.r):

(I.r)

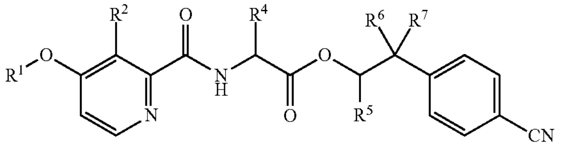

Wherein $R^1$, $R^2$, $R^4$, $R^5$, $R^6$ and $R^7$ are as defined in Table 1.

s) 150 compounds of formula (I.s):

(I.s)

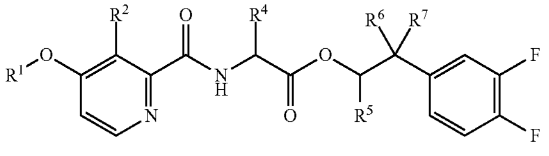

Wherein $R^1$, $R^2$, $R^4$, $R^5$, $R^6$ and $R^7$ are as defined in Table 1.

t) 150 compounds of formula (I.t):

(I.t)

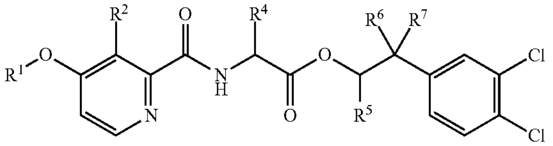

Wherein $R^1$, $R^2$, $R^4$, $R^5$, $R^6$ and $R^7$ are as defined in Table 1.

u) 150 compounds of formula (I.u):

(I.u)

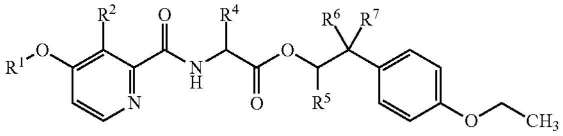

Wherein $R^1$, $R^2$, $R^4$, $R^5$, $R^6$ and $R^7$ are as defined in Table 1.

v) 150 compounds of formula (I.v):

(I.v)

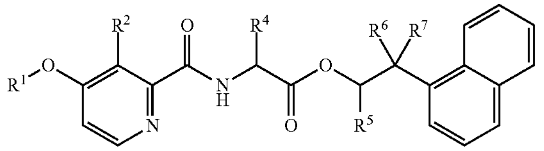

Wherein $R^1$, $R^2$, $R^4$, $R^5$, $R^6$ and $R^7$ are as defined in Table 1.

w) 150 compounds of formula (I.w):

(I.w)

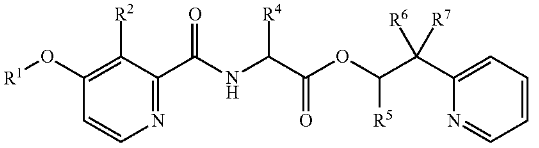

wherein $R^1$, $R^2$, $R^4$, $R^5$, $R^6$ and $R^7$ are as defined in Table 1.

x) 150 compounds of formula (I.x):

(I.x)

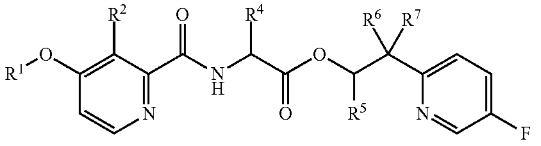

wherein $R^1$, $R^2$, $R^4$, $R^5$, $R^6$ and $R^7$ are as defined in Table 1.

y) 150 compounds of formula (I.y):

(I.y)

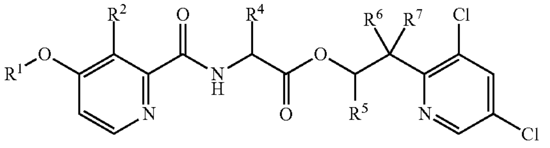

wherein $R^1$, $R^2$, $R^4$, $R^5$, $R^6$ and $R^7$ are as defined in Table z) 150 compounds of formula (I.z):

(I.z)

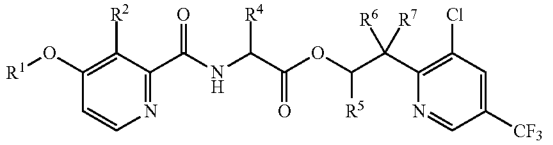

wherein $R^1$, $R^2$, $R^4$, $R^5$, $R^6$ and $R^7$ are as defined in Table 1.

aa) 150 compounds of formula (I.aa):

(I.aa)

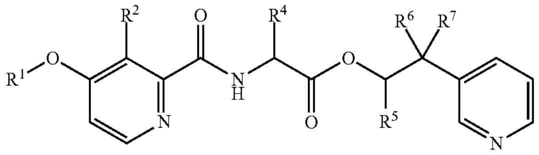

wherein $R^1$, $R^2$, $R^4$, $R^5$, $R^6$ and $R^7$ are as defined in Table 1.

ab) 150 compounds of formula (I.ab):

(I.ab)

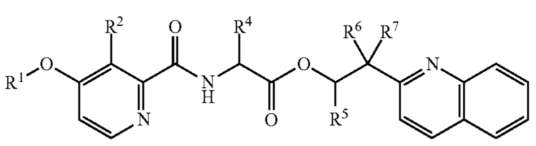

wherein $R^1$, $R^2$, $R^4$, $R^5$, $R^6$ and $R^7$ are as defined in Table 1.

ac) 150 compounds of formula (I.ac):

(I.ac)

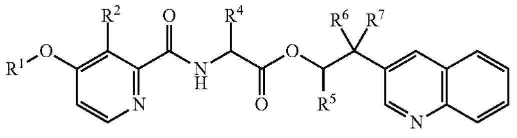

wherein $R^1$, $R^2$, $R^4$, $R^5$, $R^6$ and $R^7$ are as defined in Table 1.

ad) 150 compounds of formula (I.ad):

(I.ad)

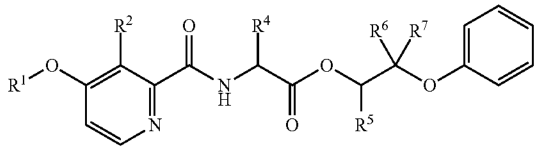

wherein $R^1$, $R^2$, $R^4$, $R^5$, $R^6$ and $R^7$ are as defined in Table 1.

ae) 150 compounds of formula (I.ae):

(I.ae)

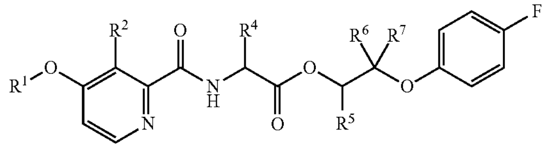

wherein $R^1$, $R^2$, $R^4$, $R^5$, $R^6$ and $R^7$ are as defined in Table 1.

af) 150 compounds of formula (I.af):

(I.af)

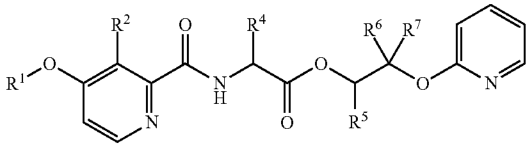

wherein $R^1$, $R^2$, $R^4$, $R^5$, $R^6$ and $R^7$ are as defined in Table 1.

ag) 150 compounds of formula (I.ag):

(I.ag)

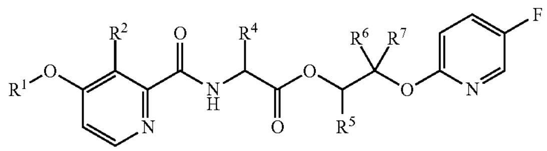

wherein $R^1$, $R^2$, $R^4$, $R^5$, $R^6$ and $R^7$ are as defined in Table 1.

ah) 150 compounds of formula (I.ah):

(I.ah)

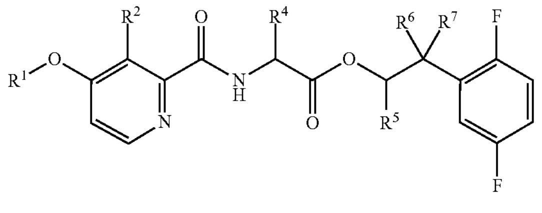

Wherein $R^1$, $R^2$, $R^4$, $R^5$, $R^6$ and $R^7$ are as defined in Table 1.

FORMULATION EXAMPLES

Wettable Powders a) b) c)

| | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

Powders for Dry Seed Treatment a) b) c)

| | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The active ingredient is thoroughly mixed with the adjuvants and the mixture is thoroughly ground in a suitable mill, affording powders that can be used directly for seed treatment.

Emulsifiable Concentrate

| | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Dusts a) b) c)

| | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable concentrate for seed treatment

| | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinyl alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

EXAMPLES

The Examples which follow serve to illustrate the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

List of Abbreviations

° C.=degrees Celsius
$CDCl_3$=chloroform-d
EDC=1-ethyl-3-(3-dimethylaminopropyl)carbodiimide
d=doublet
m=multiplet
MHz=mega hertz
mp=melting point
ppm=parts per million
s=singlet
t=triplet

EXAMPLES

Example 1: This example illustrates the preparation of 1-(1-phenylcyclopropyl)ethyl (2S)-2-[(3-hydroxy-4-methoxy-pyridine-2-carbonyl)amino]propanoate (Compound 1.a.006)

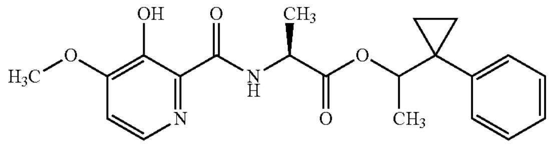 [SMILES: COc1ccnc(C(=O)N[C@@H](C)C(=O)OC(C)C2(c3ccccc3)CC2)c1O]

a) Preparation of N-methoxy-N-methyl-1-phenylcyclopropanecarboxamide 1,1'-Carbonyldiimidazole (2.5 g, 15 mmol) was added at room temperature to a solution of 1-phenylcyclopropancarboxylic acid (1.6 g, 10 mmol) in 20 ml of dichloroethane. The reaction mixture was heated to 60° C. for 4 h, then N-methoxy-N-methyl-hydroxylamine (1.7 g, 15 mmol) was added and the reaction mixture was stirred for 16 h at 60° C., then cooled to room temperature and diluted with water and dichloromethaner. The phases were separated and the aqueous phase was washed with dichloromethane. The combined organic layer was washed with water, dried over sodium sulfate and evaporated under reduced pressure, the remainder was purified by chromatography on silica gel, using ethyl acetate/cyclohexane as eluent system, to deliver N-methoxy-N-methyl-1-phenylcyclopropanecarboxamide (1.4 g, 6.7 mmol). $^1$H-NMR (400 MHz, $CDCl_3$): δ=1.13 (t, 2H), 1.44 (t, 2H), 3.12 (s, 3H), 3.20 (s, 3H), 7.20-7.36 (m, 5H).

b) Preparation of 1-(1-phenylcyclopropyl)ethanone 16 ml of a 1 M solution of methylmagnesium brmide in tetrhydrofurane were added dropwise at 0° C. to a solution of N-methoxy-N-methyl-1-phenylcyclopropanecarboxamide (1.4 g, 6.7 mmol) in 16 ml of tetrahydrofuran. The reaction mixture was stirred for 16 h at 50° C., then cooled to 0° C. and quenched by addition of saturated aqueous ammoinium chloride solution. The mixture was diluted with ethyl acetate, the phases were separated and the aqueous phase was washed with ethyl acetate. The combined organic layer was washed with water, dried over sodium sulfate and evaporated under reduced pressure, the remainder was purified by chromatography on silica gel, using ethyl acetate/cyclohexane as eluent system, to deliver 1-(1-phenylcyclopropyl)ethanone (0.9 g, 4.6 mmol)$^1$H-NMR (400 MHz, $CDCl_3$): δ=1.20 (t, 2H), 1.63 (t, 2H), 2.02 (s, 3H), 7.30-7.41 (m, 5H).

c) Preparation of 1-(1-phenylcyclopropyl)ethanol

Sodium borohydride (0.1 g, 2.7 mmol) was slowly added at 0° C. to a solution of 1-(1-phenylcyclopropyl)ethanone (0.9 g, 4.6 mmol) in 30 ml of methanol. The reaction mixture was stirred for 16 h at room temperature, then again cooled to 0° C. and quenched by addition of saturated aqueous ammonium chloride solution. The mixture was diluted with water and extracted with ethyl acetate. The organic layer was washed with water and brine, dried over sodium sulfate and evaporated under reduced pressure. The residue was purified by chromatography on silica gel, using ethyl acetate/heptane 1:3 as solvent system to deliver 1-(1-phenylcyclopropyl) ethanol (0.56 g, 3.5 mmol). $^1$H-NMR (400 MHz, $CDCl_3$): δ=0.77-0.90 (m, 4H), 1.15 (d, 3H), 3.41 (q, 1H), 7.25-7.41 (m, 5H).

d) Preparation of 1-(1-phenylcyclopropyl)ethyl (2S)-2-[(3-hydroxy-4-methoxy-pyridine-2-carbonyl) amino]propanoate (Compound 1.a.006)

1-(1-phenylcyclopropyl)ethanol (0.28 g, 1.7 mmol), 4-pyrrolidinopyridine (0.26 g, 1.7 mmol) and N-(3-dimethylaminopropyl)-N'-ethylcarbodiimide (EDC, 0.46 g, 2.9 mmol) were consecutively added at 0° C. to a suspension of (2S)-2-[(3-hydroxy-4-methoxy-pyridine-2-carbonyl)amino] propanoic acid (0.35 g, 1.5 mmol) in 18 ml of dichloromethane. The reaction mixture was stirred for 5 h at room temperature, then quenched by addition of diluted hydrochloric acid and diluted with dichloromethane. The phases were separated, the organic layer was washed with saturated aqueous sodium bicarbonate solution and brine, dried over sodium sulfate and evaporated under reduced pressure. The residue was purified by chromatography on silica gel, using ethyl acetate/cyclohexane 1:3 as solvent system to deliver 1-(1-phenylcyclopropyl)ethyl (2S)-2-[(3-hydroxy-4-methoxy-pyridine-2-carbonyl)amino]propanoate (Compound 1.a.006, 0.15 g, 0.4 mmol)$^1$H-NMR (400 MHz, $CDCl_3$): δ=0.82-0.99 (m, 4H), 1.21 (t, 3H), 1.52-1.61 (m, 3H), 3.97 (s, 3H), 4.63-4.77 (m, 2H), 6.90 (d, 1H), 7.22-7.39 (m, 5H), 8.04 (d, 1H), 8.55 (bs, 1H), 12.21 (s, 1H).

Throughout this description, temperatures are given in degrees Celsius (° C.) and "m.p." means melting point. LC/MS means Liquid Chromatography Mass Spectrometry and the description of the apparatus and the method is: (Method A: ACQUITY UPLC from Waters, Waters UPLC HSS T3, 1.8 μm particle size, 30×2.1 mm column, 0.85 mL/min., 60° C., $H_2O$/MeOH 95:5+0.05% HCOOH (90%)/$CH_3CN$+0.05% HCOOH (10%)—1.2 min.—$CH_3CN$+0.05% HCOOH (100%)—0.30 min., ACQUITY SQD Mass Spectrometer from Waters, ionization method: electrospray (ESI), Polarity: positive ions, Capillary (kV) 3.00, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650). Method B: ACQUITY UPLC from Waters, Waters UPLC HSS T3, 1.8 μm particle size, 30×2.1 mm column, 0.85 mL/min., 60° C., $H_2O$/MeOH 95:5+0.05% HCOOH (90%)/$CH_3CN$+0.05% HCOOH (10%)—2.7 min.—$CH_3CN$+0.05% HCOOH (100%)—0.30 min., ACQUITY SQD Mass Spectrometer from Waters, ionization method: electrospray (ESI), Polarity: positive ions, Capillary (kV) 3.00, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650)).

TABLE 2

LC/MS data (Rt = Retention time) for selected compounds of Table 1.

| Compound No. | Compound name | Structure | LC/MS |
|---|---|---|---|
| I.a.001 | (1,2-dimethyl-2-phenyl-propyl) (2S)-2-[(3-hydroxy-4-methoxy-pyridine-2-carbonyl)amino]propanoate | 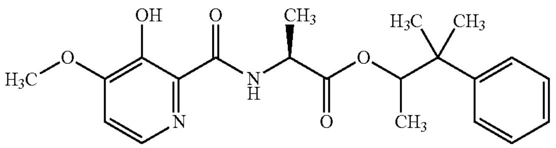 [SMILES: COc1ccnc(C(=O)N[C@@H](C)C(=O)OC(C)C(C)(C)c2ccccc2)c1O] | (A) Rt = 1.09 min; MS: m/z = 387 (M + 1) |
| I.a.006 | 1-(1-phenylcyclopropyl)-ethyl (2S)-2-[(3-hydroxy-4-methoxy-pyridine-2-carbonyl)amino]propanoate | 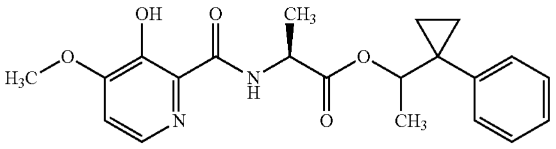 [SMILES: COc1ccnc(C(=O)N[C@@H](C)C(=O)OC(C)C2(c3ccccc3)CC2)c1O] | (A) Rt = 1.07 min; MS: m/z = 385 (M + 1) |

TABLE 2-continued

LC/MS data (Rt = Retention time) for selected compounds of Table 1.

| Compound No. | Compound name | Structure | LC/MS |
|---|---|---|---|
| I.a.010 | 1-(1,2-diphenylcyclo-propyl)ethyl (2S)-2-[(3-hydroxy-4-methoxy-pyridine-2-carbonyl)-amino]propanoate | 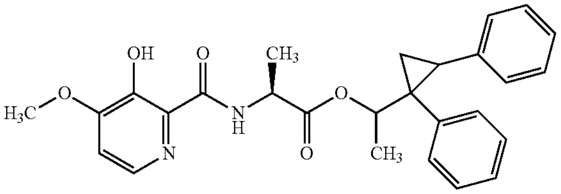 [SMILES: COc1ccnc(C(=O)N[C@@H](C)C(=O)OC(C)C2(c3ccccc3)CC2c2ccccc2)c1O] | (B) Rt = 1.92 min, 1.95 min, 1.97 min; MS: m/z = 461 [M + 1] |
| I.a.015 | 1-(1-phenylcyclohexyl)-ethyl (2S)-2-[(3-hydroxy-4-methoxy-pyridine-2-carbonyl)amino]propanoate | 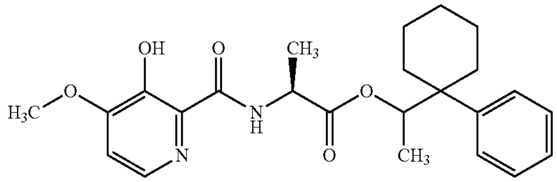 [SMILES: COc1ccnc(C(=O)N[C@@H](C)C(=O)OC(C)C2(c3ccccc3)CCCCC2)c1O] | (A) Rt = 1.21 min; MS: m/z = 427 (M + 1) |
| I.d.006 | 1-[1-(3-bromophenyl)-cyclopropyl]ethyl (2S)-2-[(3-hydroxy-4-methoxy-pyridine-2-carbonyl)amino]propanoate | 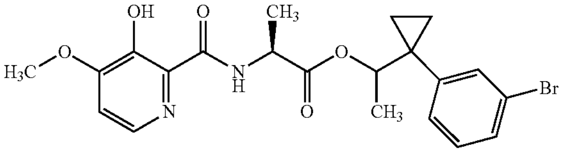 [SMILES: COc1ccnc(C(=O)N[C@@H](C)C(=O)OC(C)C2(c3cccc(Br)c3)CC2)c1O] | (A) Rt = 1.15 min; MS: m/z = 463 (M + 1) |
| I.j.001 | [2-(4-fluorophenyl)-1,2-dimethyl-propyl] (2S)-2-[(3-hydroxy-4-methoxy-pyridine-2-carbonyl)-amino]propanoate | 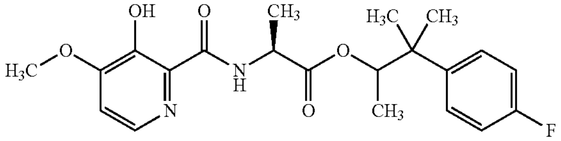 [SMILES: COc1ccnc(C(=O)N[C@@H](C)C(=O)OC(C)C(C)(C)c2ccc(F)cc2)c1O] | (B) Rt = 1.75 min; MS: m/z = 405 (M + 1) |
| I.j.010 | 1-[1-(4-fluorophenyl)-2-phenyl-cyclopropyl]-ethyl (2S)-2-[(3-hydroxy-4-methoxy-pyridine-2-carbonyl)-amino]propanoate | 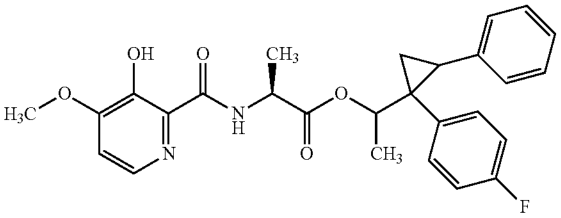 [SMILES: COc1ccnc(C(=O)N[C@@H](C)C(=O)OC(C)C2(c3ccc(F)cc3)CC2c2ccccc2)c1O] | (B) Rt = 1.93 min, 1.97 min; MS: m/z = 479 (M + 1) |
| I.j.011 | 1-[1,2-bis(4-fluoro-phenyl)cyclopropyl]-ethyl (2S)-2-[(3-hydroxy-4-methoxy-pyridine-2-carbonyl)-amino]propanoate | 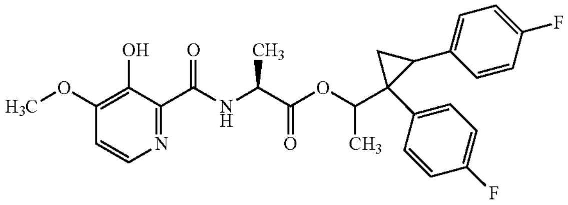 [SMILES: COc1ccnc(C(=O)N[C@@H](C)C(=O)OC(C)C2(c3ccc(F)cc3)CC2c2ccc(F)cc2)c1O] | (B) Rt = 1.95 min, 1.97 min; MS: m/z = 496 (M + 1) |
| I.k.001 | [2-(4-chlorophenyl)-1,2-dimethyl-propyl] (2S)-2-[(3-hydroxy-4-methoxy-pyridine-2-carbonyl)amino]propanoate | 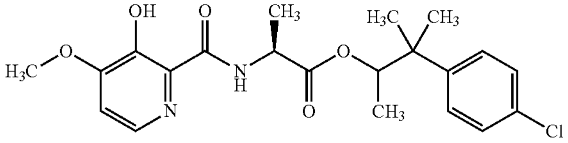 [SMILES: COc1ccnc(C(=O)N[C@@H](C)C(=O)OC(C)C(C)(C)c2ccc(Cl)cc2)c1O] | (B) Rt = 1.89 min; MS: m/z = 421 (M + 1) |
| I.k.006 | 1-[1-(4-chlorophenyl)-cyclopropyl]ethyl (2S)-2-[(3-hydroxy-4-methoxy-pyridine-2-carbonyl)amino]propanoate | 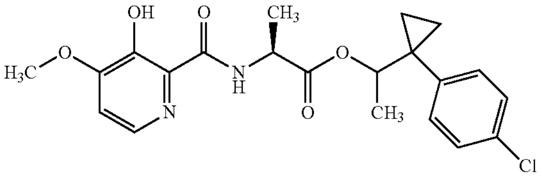 [SMILES: COc1ccnc(C(=O)N[C@@H](C)C(=O)OC(C)C2(c3ccc(Cl)cc3)CC2)c1O] | (A) Rt = 1.12 min; MS: m/z = 419 (M + 1) |

TABLE 2-continued

LC/MS data (Rt = Retention time) for selected compounds of Table 1.

| Compound No. | Compound name | Structure | LC/MS |
|---|---|---|---|
| I.k.012 | 1-[1-(4-chlorophenyl)-cyclobutyl]ethyl (2S)-2-((3-hydroxy-4-methoxy-pyridine-2-carbonyl)-amino]propanoate | 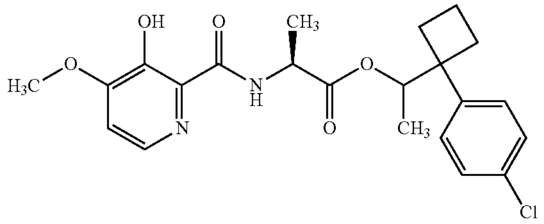 [SMILES: COc1ccnc(C(=O)N[C@@H](C)C(=O)OC(C)C2(c3ccc(Cl)cc3)CCC2)c1O] | (A) Rt = 1.17 min; MS: m/z = 433 (M + 1) |
| I.k.014 | 1-[1-(4-chlorophenyl)-cyclopentyl]ethyl (2S)-2-[(3-hydroxy-4-methoxy-pyridine-2-carbonyl)amino]propanoate | 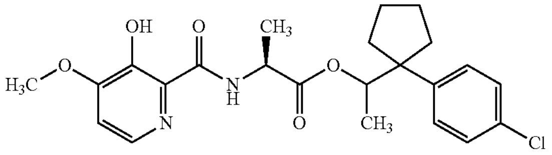 [SMILES: COc1ccnc(C(=O)N[C@@H](C)C(=O)OC(C)C2(c3ccc(Cl)cc3)CCCC2)c1O] | (A) Rt = 1.22 min; MS: m/z = 447 (M + 1) |
| I.k.015 | 1-[1-(4-chlorophenyl)-cyclohexyl]ethyl (2S)-2-[(3-hydroxy-4-methoxy-pyridine-2-carbonyl)amino]propanoate | 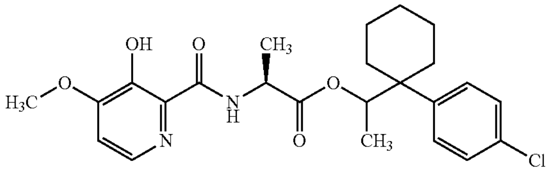 [SMILES: COc1ccnc(C(=O)N[C@@H](C)C(=O)OC(C)C2(c3ccc(Cl)cc3)CCCCC2)c1O] | (A) Rt = 1.25 min; MS: m/z = 462 (M + 1) |
| I.k.075 | 1-[1-(4-chlorophenyl)-cyclohexyl]ethyl (2S)-2-[(3-acetoxy-4-methoxy-pyridine-2-carbonyl)-amino]propanoate | 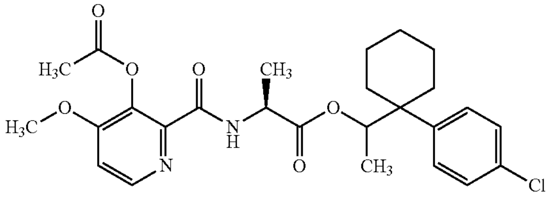 [SMILES: COc1ccnc(C(=O)N[C@@H](C)C(=O)OC(C)C2(c3ccc(Cl)cc3)CCCCC2)c1OC(C)=O] | (B) Rt = 2.13 min; MS: m/z = 503 (M + 1) |
| I.m.001 | [2-(4-bromophenyl)-1,2-dimethyl-propyl] (2S)-2-[(3-hydroxy-4-methoxy-pyridine-2-carbonyl)amino]propanoate | 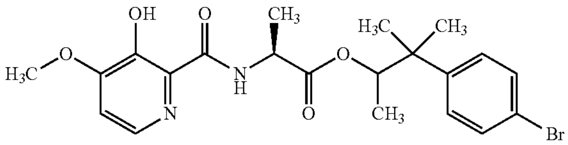 [SMILES: COc1ccnc(C(=O)N[C@@H](C)C(=O)OC(C)C(C)(C)c2ccc(Br)cc2)c1O] | (A) Rt = 1.17 min; MS: m/z = 465 (M + 1) |
| I.m.006 | 1-[1-(4-bromophenyl)-cyclopropyl]ethyl (2S)-2-[(3-hydroxy-4-methoxy-pyridine-2-carbonyl)amino]propanoate | 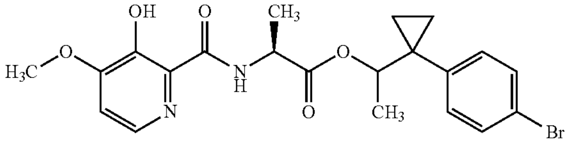 [SMILES: COc1ccnc(C(=O)N[C@@H](C)C(=O)OC(C)C2(c3ccc(Br)cc3)CC2)c1O] | (B) Rt = 1.88 min; MS: m/z = 463 (M + 1), 465 (M + 3) |
| I.m.012 | 1-[1-(4-bromophenyl)-cyclobutyl]ethyl (2S)-2-[(3-hydroxy-4-methoxy-pyridine-2-carbonyl)amino]propanoate | 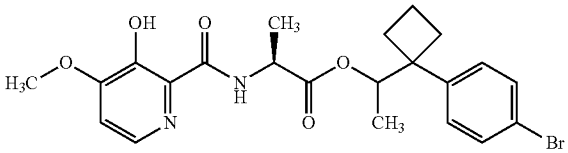 [SMILES: COc1ccnc(C(=O)N[C@@H](C)C(=O)OC(C)C2(c3ccc(Br)cc3)CCC2)c1O] | (A) Rt = 1.20 min; MS: m/z = 477 (M + 1) |
| I.o.014 | 1-[1-[4-(trifluoromethyl)-phenyl]cyclopentyl]ethyl (2S)-2-[(3-hydroxy-4-methoxy-pyridine-2-carbonyl)amino]prapanoate | 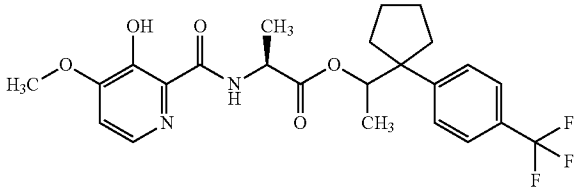 [SMILES: COc1ccnc(C(=O)N[C@@H](C)C(=O)OC(C)C2(c3ccc(C(F)(F)F)cc3)CCCC2)c1O] | (B) Rt = 2.08 min; MS: m/z = 481 (M + 1) |

TABLE 2-continued

LC/MS data (Rt = Retention time) for selected compounds of Table 1.

| Compound No. | Compound name | Structure | LC/MS |
|---|---|---|---|
| I.q.006 | 1-[1-[4-(trifluoro-methoxy)phenyl]cyclo-propyl]ethyl (2S)-2-[(3-hydroxy-4-methoxy-pyridine-2-carbonyl)amino]propanoate | 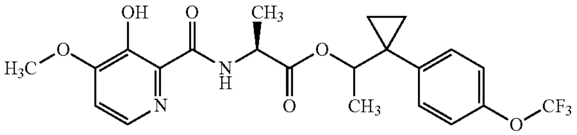 [SMILES: COc1ccnc(C(=O)N[C@@H](C)C(=O)OC(C)C2(c3ccc(OC(F)(F)F)cc3)CC2)c1O] | (B) Rt = 1.95 min; MS: m/z = 470 (M +1) |
| I.t.006 | 1-[1-(3,4-dichloro-phenyl)cyclopropyl]-ethyl (2S)-2-[(3-hydroxy-4-methoxy-pyridine-2-carbonyl)-amino]propanoate | 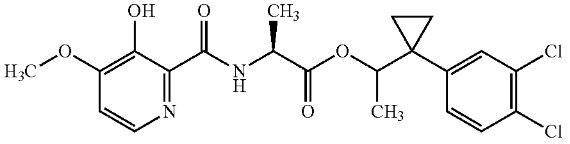 [SMILES: COc1ccnc(C(=O)N[C@@H](C)C(=O)OC(C)C2(c3ccc(Cl)c(Cl)c3)CC2)c1O] | (B) Rt = 1.96 min; MS: m/z = 453 (M + 1) |
| I.u.007 | 1-[1-(4-ethoxyphenyl)-2,2-difluorocyclopropyl]-ethyl (2S)-2-[(3-hydroxy-4-methoxy-pyridine-2-carbonyl)amino]propanoate | 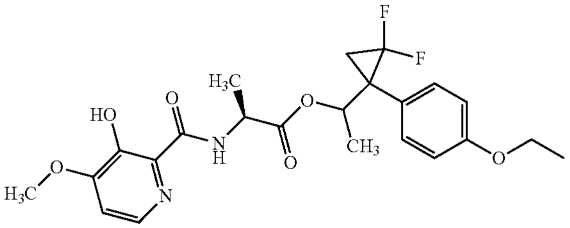 [SMILES: CCOc1ccc(C2(C(C)OC(=O)[C@H](C)NC(=O)c3nccc(OC)c3O)CC2(F)F)cc1] | (B) Rt = 1.69 min; MS: m/z = 466 (M + 1) |
| I.v.006 | 1-[1-(1-naphthyl)cyclo-propyl]ethyl (2S)-2-[(3-hydroxy-4-methoxy-pyridine-2-carbonyl)-amino]propanoate | 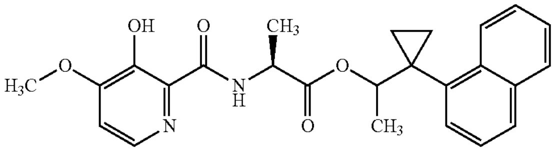 [SMILES: COc1ccnc(C(=O)N[C@@H](C)C(=O)OC(C)C2(c3cccc4ccccc34)CC2)c1O] | (B) Rt = 1.90 min; MS: m/z = 435 (M + 1) |
| I.v.010 | 1-[1-(1-naphthyl)-2-phenyl-cyclopropyl]-ethyl (2S)-2-[(3-hydroxy-4-methoxy-pyridine-2-carbonyl)-amino]propanoate | 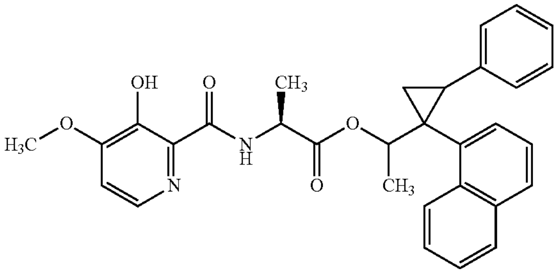 [SMILES: COc1ccnc(C(=O)N[C@@H](C)C(=O)OC(C)C2(c3cccc4ccccc34)CC2c2ccccc2)c1O] | (B) Rt = 2.06 min, 2.09 min, 2.11 min; MS: m/z = 511 (M + 1) |
| I.v.011 | 1-[2-(4-fluorophenyl)-1-(1-naphthyl)cyclo-propyl]ethyl (2S)-2-[(3-hydroxy-4-methoxy-pyridine-2-carbonyl)amino]-propanoate | 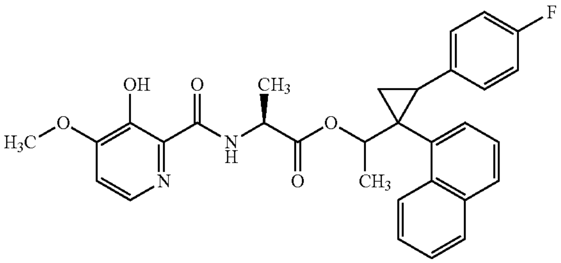 [SMILES: COc1ccnc(C(=O)N[C@@H](C)C(=O)OC(C)C2(c3cccc4ccccc34)CC2c2ccc(F)cc2)c1O] | (B) Rt = 2.08 min, 2.10 min, 2.11 min; MS: m/z = 529 (M + 1) |
| I.v.066 | 1-[1-(1-naphthyl)cyclo-propyl]ethyl (2S)-2-[(3-acetoxy-4-methoxy-pyridine-2-carbonyl)-amino]propanoate | 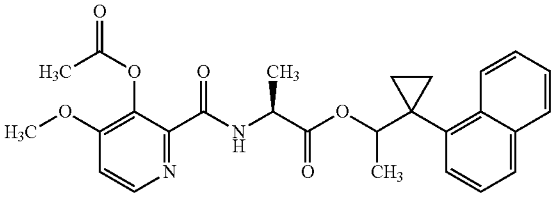 [SMILES: COc1ccnc(C(=O)N[C@@H](C)C(=O)OC(C)C2(c3cccc4ccccc34)CC2)c1OC(C)=O] | (B) Rt = 1.92 min; MS: m/z = 477 (M + 1) |

TABLE 2-continued

| LC/MS data (Rt = Retention time) for selected compounds of Table 1. | | | |
|---|---|---|---|
| Compound No. | Compound name | Structure | LC/MS |
| I.ah.001 | [2-(2,5-difluoro-phenyl)-1,2-dimethyl-propyl] (2S)-2-[(3-hydroxy-4-methoxy-pyridine-2-carbonyl)-amino]propanoate | 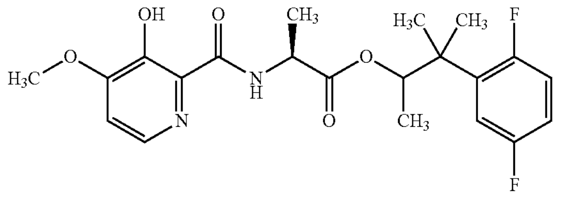 [SMILES: COc1ccnc(C(=O)N[C@@H](C)C(=O)OC(C)C(C)(C)c2cc(F)ccc2F)c1O] | (B) Rt = 1.76 min; MS: m/z = 424 (M + 1) |

BIOLOGICAL EXAMPLES

*Blumeria graminis* f. sp. *tritici* (*Erysiphe raminis* f. sp. *tritici*)/wheat/leaf disc preventative (Powdery Mildew on Wheat)

Wheat leaf segments cv. Kanzler are placed on agar in a multiwell plate (24-well format) and sprayed with the test compound formulated with DMSO and Tween20 and diluted in water. The leaf disks are inoculated by shaking powdery mildew infected plants above the test plates 1 day after application. The inoculated leaf disks are incubated at 20° C. and 60% rh under a light regime of 24 h darkness followed by 12 h light/12 h darkness in a climate chamber and the activity of a compound is assessed as percent disease control compared to untreated when an appropriate level of disease damage appears on untreated check leaf segments (6-8 days after application).

Compounds I.k.012, I.k.015 and I.m.012 at 200 ppm in the formulation give at least 80% disease control in this test when compared to untreated control leaf disks under the same conditions, which show extensive disease development.

*Botryotinia fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

Compounds I.a.001, I.a.006, I.a.010, I.a.015, I.d.006, I.j.001, I.k.006, I.k.012 I.k.014, I.k.015, I.m.001, I.m.012, I.q.006, I.t.006, I.u.007, and I.v.066 at 200 ppm in the formulation give at least 80% disease control in this test when compared to untreated control leaf disks under the same conditions, which show extensive disease development.

*Glomerella lacenarium* (*Colletotrichum lacenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

Compounds I.a.010, I.a.015, I.d.006, I.j.001, I.j.010, I.j.011, I.k.012, I.k.014, I.k.015, I.k.075, I.m.001, I.m.012, I.q.006, I.t.006, I.u.007, I.v.006, I.v.010, I.v.011, I.v.066 and I.ah.001 at 200 ppm in the formulation give at least 80% disease control in this test when compared to untreated control leaf disks under the same conditions, which show extensive disease development.

*Magnaporthe risea* (*Pyricularia Oryzae*)/Rice/Leaf Disc Preventative (Rice Blast)

Rice leaf segments cv. *Ballila* are placed on agar in a multiwell plate (24-well format) and sprayed with the test compound formulated with DMSO and Tween20 and diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5-7 days after application).

Compounds I.a.006, I.a.010, I.a.015, I.k.012, I.k.014, I.k.075, I.m.001, I.m.012, I.q.006, I.t.006, I.u.007, I.v.066 and I.ah.001 at 200 ppm in the formulation give at least 80% disease control in this test when compared to untreated control leaf disks under the same conditions, which show extensive disease development

*Monocraphella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.a.001, I.a.006 I.k.006, I.a.010, I.a.015, I.d.006, I.j.001, I.j.011, I.k.012 I.k.014, I.k.015, I.m.001, I.m.012, I.q.006, I.t.006, I.u.007, I.v.006, I.v.066 and I.ah.001 at 200 ppm in the formulation give at least 80% disease control in this test when compared to untreated control leaf disks under the same conditions, which show extensive disease development.

*Mycosphaerella arachidis* (*Cercospora arachidicola*)/Liquid Culture (Early Leaf Spot)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.a.001, I.a.006, I.k.006, I.a.010, I.a.015, I.d.006, I.j.001, I.j.010, I.j.011, I.k.012, I.k.014, I.k.015, I.k.075, I.m.001, I.m.012, I.q.006, I.t.006, I.v.006, I.v.010, I.v.011, I.v.066 and I.ah.001 at 200 ppm in the formulation give at least 80% disease control in this test when compared to untreated control leaf disks under the same conditions, which show extensive disease development.

*Mycosphaerella* Raminicola (*Septoria tritici*)/Liquid Culture (*Septoria* Blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4 to 5 days after application.

Compounds I.a.001, I.a.006, I.a.010, I.a.015, I.d.006, I.j.001, I.j.010, I.j.011, I.k.006, I.k.012, I.k.014, I.k.015, I.k.075, I.m.001, I.m.012, I.q.006, I.t.006, I.u.007, I.v.006, I.v.010, I.v.011, I.v.066 and I.ah.001 at 200 ppm in the formulation give at least 80% disease control in this test when compared to untreated control leaf disks under the same conditions, which show extensive disease development.

*Phaeosphaeria Nodorum* (*Septoria nodorum*)/Wheat/Leaf Disc Preventative (Glume Blotch)

Wheat leaf segments cv. Kanzler are placed on agar in a multiwell plate (24-well format) and sprayed with the formulated test compound diluted in water. The leaf disks are inoculated with a spore suspension of the fungus 2 days after application. The inoculated test leaf disks are incubated at 20° C. and 75% rh under a light regime of 12 h light/12 h darkness in a climate cabinet and the activity of a compound is assessed as percent disease control compared to untreated when an appropriate level of disease damage appears in untreated check leaf disks (5-7 days after application).

Compound I.a.001, I.a.010, I.a.015, I.k.006, I.k.012, I.k.015, I.k.075, I.m.001, I.v.006, I.v.066 and I.ah.001 at 200 ppm in the formulation give at least 80% disease control in this test when compared to untreated control leaf disks under the same conditions, which show extensive disease development.

*Puccinia recondita* f. Sp. *Tritici*/Wheat/Leaf Disc Preventative (Brown Rust)

Wheat leaf segments cv. Kanzler are placed on agar in multiwell plates (24-well format) and sprayed with the formulated test compound diluted in water. The leaf disks are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application).

Compound I.a.001, I.a.006, I.a.010, I.a.015, I.d.006, I.j.001, I.j.010, I.j.011, I.k.006, I.k.012, I.k.014, I.k.015, I.k.075, I.m.001, I.m.012, I.q.006, I.t.006, I.u.007, I.v.006, I.v.010, I.v.011, I.v.066 and I.ah.001 at 200 ppm in the formulation give at least 80% disease control in this test when compared to untreated control leaf disks under the same conditions, which show extensive disease development.

What is claimed is:

1. A compound of formula (I):

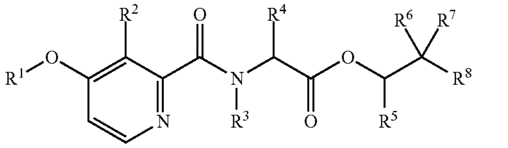

(I)

wherein, $R^1$ is $C_1$-$C_{12}$alkyl or $C_1$-$C_6$haloalkyl;

$R^2$ is hydroxy, $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy or $C_2$-$C_6$acyloxy$C_1$-$C_6$haloalkoxy;

$R^3$ is hydrogen, $C_1$-$C_6$alkyl, $C_1$-$C_6$alkoxy or $C_3$-$C_8$cycloalkyl;

$R^4$ and $R^5$ are independently $C_1$-$C_{12}$alkyl, $C_3$-$C_8$cycloalkyl, $C_1$-$C_6$haloalkyl, $C_1$-$C_6$alkoxy$C_1$-$C_6$alkyl or $C_3$-$C_8$halocycloalkyl;

$R^6$ and $R^7$ are independently $C_1$-$C_4$alkyl; or $R^6$ and $R^7$ together with the carbon atom to which they are attached form a $C_3$-$C_8$cycloalkyl ring which is optionally substituted by 1, 2 or 3 substituents, which may be the same or different, selected from $R^9$, or is optionally substituted by a single substituent which is $R^{10}$, or is optionally substituted by 1 or 2 substituents, which may be the same or different, selected from $R^9$ and a single substituent which is $R^{10}$;

$R^8$ is phenyl, phenoxy, naphthyl, naphthyloxy, heteroaryl or heteroaryloxy, wherein the heteroaryl moiety is a 5- or 6-membered aromatic ring which comprises 1, 2, 3 or 4 heteroatoms individually selected from N, O and S, heterodiaryl or heterodiaryloxy, wherein the heterodiaryl moiety is a 9- or 10-membered bicyclic aromatic system which comprises 1, 2, 3 or 4 heteroatoms individually selected from N, O and S, wherein each phenyl, naphthyl, heteroaryl or heterodiaryl is optionally substituted by 1, 2 or 3 substituents, which may be the same or different, selected from $R^9$;

$R^9$ is halogen, cyano, $C_1$-$C_4$alkyl, $C_1$-$C_4$haloalkyl, $C_1$-$C_4$alkoxy, $C_1$-$C_4$haloalkoxy; and $R^{10}$ is phenyl or cyclopropyl each optionally substituted by 1, 2 or 3 substituents, which may be the same or different, selected from fluoro, chloro, bromo, cyano, methyl, ethyl, difluoromethyl, trifluoromethyl, methoxy, ethoxy, difluoromethoxy, trifluoromethoxy; or a salt or an N-oxide thereof.

2. The compound according to claim 1, wherein $R^1$ is methyl or ethyl.

3. The compound according to claim 1, wherein $R^2$ is hydroxy, acetoxy, propanoyloxy, acetoxymethoxy, propanoyloxymethoxy, 2-methyl-propanoyloxymethoxy.

4. The compound according to claim 1, wherein $R^2$ is hydroxy.

5. The compound according to claim 1, wherein $R^3$ is hydrogen.

6. The compound according to claim 1, wherein $R^4$ is methyl or ethyl and $R^5$ is methyl or ethyl.

7. The compound according to claim 1, wherein $R^6$ and $R^7$ together with the carbon atom to which they are attached form a $C_3$-$C_6$cycloalkyl ring which is optionally substituted by 1, 2 or 3 substituents, which may be the same or different, selected from $R^9$, or is optionally substituted by a single substituent which is $R^{10}$, or is optionally substituted by 1 or 2 substituents, which may be the same or different, selected from $R^9$ and a single substituent which is $R^{10}$.

8. The compound according to claim 1, wherein $R^8$ is phenyl, naphthyl, furyl, benzofuryl, thienyl, benzothienyl, pyrrolyl, indolyl, pyrazolyl, indazolyl, imidazolyl, benzimidazolyl, thiazolyl, benzothiazolyl, oxazolyl, benzoxazolyl, pyridyl, quinolinyl, isoquinolinyl, pyridazinyl, cinnolinyl, pyrimidinyl, quinazolinyl, pyrazinyl, phenoxy, naphthyloxy, pyridyloxy or quinolinyloxy, optionally substituted by 1, 2 or 3 substituents, which may be the same or different, selected from $R^9$.

9. The compound according to claim 1, wherein $R^8$ is phenyl, naphthyl, thienyl, indolyl, pyridyl, quinolinyl, pyridazinyl, pyrimidinyl, pyrazinyl, phenoxy, pyridyloxy or quinolinyloxy optionally substituted by 1 or 2 substituents, which may be the same or different, selected from $R^9$.

10. The compound according to claim 1, wherein $R^8$ is phenyl, thienyl, pyridyl, phenoxy or pyridyloxy optionally substituted by a single substituent selected from $R^9$.

11. An agrochemical composition comprising a fungicidally effective amount of a compound of formula (I) according to claim 1, and an agrochemically-acceptable carrier or diluent.

12. The composition according to claim 11, further comprising at least one additional active ingredient.

13. A method of controlling or preventing infestation of useful plants by phytopathogenic microorganisms, wherein a fungicidally effective amount of a compound of formula (I) according to claim 1, or a composition comprising this compound as active ingredient, is applied to the plants, to parts thereof or the locus thereof.

14. The compound according to claim 1, wherein $R^6$ and $R^7$ are methyl.

* * * * *